(12) United States Patent
Haruna et al.

(10) Patent No.: US 6,172,752 B1
(45) Date of Patent: Jan. 9, 2001

(54) METHOD AND APPARATUS FOR SIMULTANEOUSLY INTERFEROMETRICALLY MEASURING OPTICAL CHARACTERISTICS IN A NONCONTACT MANNER

(75) Inventors: Masamitsu Haruna, Toyonaka; Hideki Maruyama, Chikushino, both of (JP)

(73) Assignee: Matsushita Electric Industrial Co., Ltd., Kadoma (JP)

(*) Notice: Under 35 U.S.C. 154(b), the term of this patent shall be extended for 0 days.

(21) Appl. No.: 08/906,392

(22) Filed: Aug. 5, 1997

(30) Foreign Application Priority Data

Aug. 5, 1996 (JP) .................................. 8-205645
Mar. 21, 1997 (JP) .................................. 9-067673

(51) Int. Cl.⁷ ..................................... G01B 9/02

(52) U.S. Cl. ........................ 356/357; 356/351; 356/360; 356/361

(58) Field of Search .................. 356/345, 349, 356/355, 357, 359, 360, 361, 351

(56) References Cited

U.S. PATENT DOCUMENTS 5,459,570 * 10/1995 Swanson et al. ............... 356/345
5,465,147 * 11/1995 Swanson ........................ 356/360

FOREIGN PATENT DOCUMENTS 63-128210   6/1988  (JP) .
64-75902    3/1989  (JP) .
317505      1/1991  (JP) .

OTHER PUBLICATIONS

Polarization Analysis, 2,4, pp. 256 to 264 of Optic Handbook.

"New Measurement System for Fault Location In Optical Waveguide Devices Based on an Interferometric Technique", Applied Optics, 1087, vol. 26, No. 9, pp. 1603 to 1606.

"Optical Coherence–Domain Reflectometry: A New Optical Evaluation Technique", Optics Letters, vol. 12, 1987, No. 3, pp. 158 to 160.

"Submillimeter Optical Reflectometry" vol. 7, 1989, No. 8, pp. 1225 to 1233.

"Optical Coherence Tomography", Science, vol. 254, pp. 1178–1181.

(List continued on next page.)

* cited by examiner

Primary Examiner—Samuel A. Turner
(74) Attorney, Agent, or Firm—Stevens, Davis, Miller & Mosher, L.L.P.

(57) ABSTRACT

Light from a light source is converged by a converging lens and is irradiated to an object to be measured through a converging lens, the object to be measured or the converging lens and the reference light mirror are displaced so as to maximize intensities of interference light at the reference light mirror and the front and rear surfaces of the object to be measured, and displaced distances of the object to be measured or the converging lens and the reference light mirror at a position where an intensity of interference light becomes maximum at the rear surface and a position where an intensity of interference light becomes maximum are obtained in order to simultaneously measure a refractive index and a thickness of the object to be measured. With this arrangement, simultaneous measurement of a phase index and a thickness of an object to be measured, simultaneous measurement of a birefringence and a thickness of an object to be measured, and a phase index and a group index of an object to be measured can be carried out.

26 Claims, 12 Drawing Sheets

OTHER PUBLICATIONS

"Optical Coherence Microscopy in Scattering Media", Optics Letters, vol. 19, 1994, No. 8, pp. 590 to 592.

"Eye–length Measurement by Interferometry with Partially Coherent Light", Optics Letters, vol. 13, 1988, No. 3, pp. 186 to 188.

"Measurement of the Thickness of Fundus Layers by Partial Coherence Tomography", Vol. 34, 1955, No. 3, pp. 701–710.

"Detection/visualization of inner structure of a biological body by the low coherent light interferometry I", $56^{th}$ Scientific Lectured by Applied Physics Association, Autumn 1995, 26a–SN–11.

$\Delta L_1 = nt - z_1$
$= X_{R1} - X_{F1}$ $\Delta L_2 = nt$
$= X_{R2} - X_{F2}$

PHASE REFRACTIVE INDEX DEPENDENCY OF WAVELENGTH DISPERSION

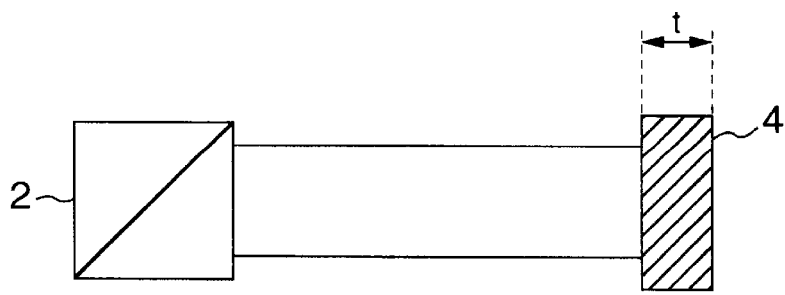
FIG.13a
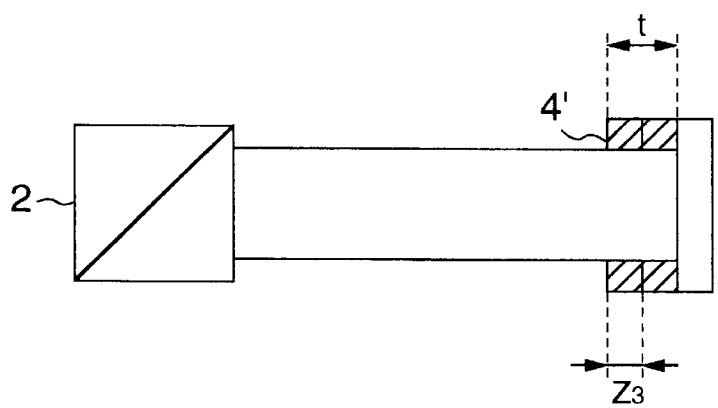
FIG.13b
FIG.13c    FIG.13d
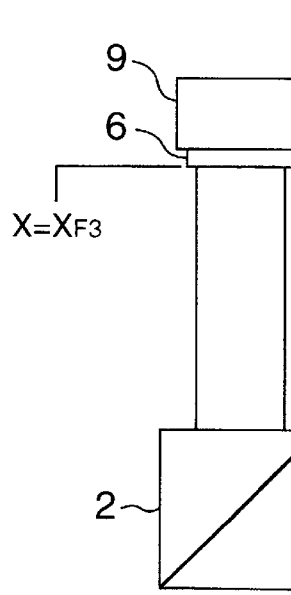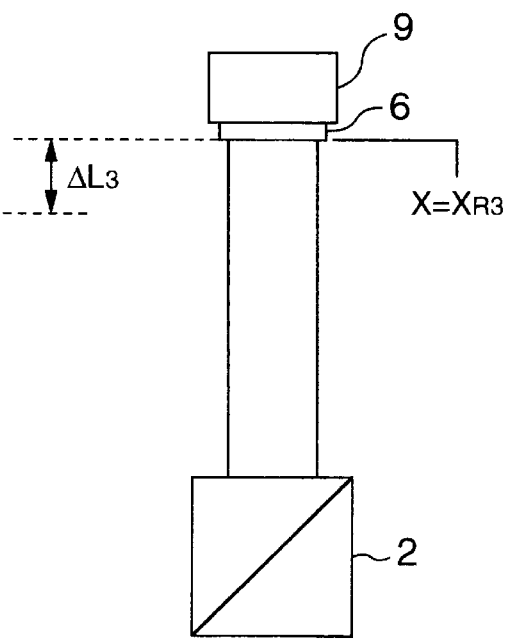

METHOD AND APPARATUS FOR SIMULTANEOUSLY INTERFEROMETRICALLY MEASURING OPTICAL CHARACTERISTICS IN A NONCONTACT MANNER

BACKGROUND OF THE INVENTION

The present invention relates to a method of and a device for simultaneously measuring a refractive index and a thickness of a medium, a method of and a device for measuring a birefringence of a medium, a method of and a device for simultaneously measuring a birefringence and a thickness of a medium, a method of and a device for simultaneously measuring a phase index and a group index of a medium, and a method of evaluating a curing condition or a degree of hardness of hardenable resin with the use of these methods and devices.

A method of measuring an optical characteristic such as a refractive index n (=phase index np), a birefringence, a thickness or the like of medium in a noncontact manner, is one of most basic technology in the optical field. The most typical one is a method which utilizes an elipsometer (automatic polarization analyzing device refer to Polarization Analysis, 2, 4, pages 256 to 264 of "Optic Handbook" edited by Hiroshi Kobota, issued by Asakura Book Store), and which is carried out by measuring a difference between phase variations of P-polarization and S-polarization of reflecting light obtained by projecting light obliquely to a medium (thin film) to be measured, that is, a polarizing condition of light reflected on the surface of a medium is observed so as to measure a refractive index n and the thickness t of a substrate or a thin film deposited on the surface thereof. Further, as disclosed in, for example, Japanese Patent Laid-Open No. 64-75902, Japanese Patent Laid-Open No. 63-128210 and Japanese Patent Laid-Open No. 3-17505, a reflection analyzing method for measuring a film thickness, a refractive index n and an absorption coefficient of a medium with the use of a reflectance factor has been also used. The reflectance analyzing method disclosed in the Japanese Patent Laid-Open No. 64-75902 or the Japanese Patent Laid-Open No. 63-128210 measures a variation in the intensity of reflecting light which is caused by a variation in incident angle of a measuring light beam, that is, an incident angle depending characteristic of the reflecting light, and uses three extreme values of incident angles so as to obtain a characteristic value of a thin film. A reflectance analyzing method disclosed in the Japanese Laid-Open Patent No. 3-17505 obtains a characteristic value of a thin film from an incident angle depending characteristic of a reflected light intensity obtained by detecting a light intensity in the rear of a detecting lens.

Apparatuses for carrying out the above-mentioned methods must have a high degree of accuracy, and accordingly are prosperously used for studying surfaces or thin films. However, these apparatuses themselves are expensive, and further, can merely measure an average refractive index n and thickness t in a part (having a diameter of 1 mm) irradiated with a collimated beam. Moreover, the thickness which can be actually measured is up to about 10 $\mu$m, that is, a thickness exceeding this value cannot be measured. In addition to the above-mentioned methods, methods of measuring a refractive index of a medium with the use of a prism, a refractive index n and a thickness t of a thin film through light guide mode excitation, are also used, but the use of these methods is limited by such a condition that a surface to be measured is flat and smooth. There has been a such a demand that a refractive index n (including a birefringence)and a thickness t of a medium including inorganic and organic materials, and a spatial distribution thereof, should precisely be measured, in methods of mainly measuring a thin film in the optical field. Further, at present, a gel fraction (a ratio between an initial weight of a sample to be measured and a variation in the weight of the sample after a solvent is extracted by using methyl-ethyl ketone or the like) is most typically used as an index for evaluating several kinds of hardenable resin (such as those which are ultraviolet-hardenable, thermo-hardenable, catalyst-hardenable, and electron-beam hardenable). However, such an evaluation uses a destruction test which requires a long time for preparation and valuation of a sample.

In view of the above-mentioned circumstances, the present invention proposes the following methods, basically using an interference optical system including a low coherence light source: a method of precisely and simultaneously measuring a phase index np and a thickness t of a medium through irradiation of a focused light beam, a method of precisely measuring a birefringence of a medium without the necessity of polarization control of a polarizer, an analyzer, a polarizing rotator or the like, and a method of precisely and simultaneously measuring a phase index np and a group index ng, and as well a method of evaluating a hardenability or a hardness of resin with the use of the above-mentioned methods.

A Michelson interferometer using a low coherence light source which can recognize a reflecting surface along a light propagation axis with a resolution (up to 10 $\mu$m) which is determined by a coherence length $2\Delta lc$ ($=\ln(2)(2/\pi)(\lambda c^2/\Delta\lambda)$, where $\lambda c$ is a center wavelength of a light source, $\Delta\lambda$ is a full width at half maximum (FWHM) of a spectrum of a light source), has been used as an effective diagnosing method in a microarea (refer to (2): "New Measurement System for Fualt Location In Optical Waveguide Devices based on an Interferometric Technique" by K. Takada, I. Yokohama, K, Chida and J. Noda, Applied Optics, 1087, Vol. 26, No. 9. Pages 1,603 to 1,606; (3): "Optical Coherence-Domain Reflectometry; a New Optical Evaluation Technique" by R. C. Youngquist, S. Carr and D. E. N. Davies, Optics Letters, Vol. 12, 1987, No. 3, pages 158 to 160; and (4): "Submillimeter Optical Refletometory" by H. H. Gilgen, R. P. Novak, R. P. Salathe, and W. Hodel and P. Beaud, J. Lightwave Technology, vol. 7. 1989, No. 8, pages 1,225 to 1,233).

Recently, even in the field of biological optical diagnosis, the above-mentioned low coherence optical interferometry has attracted great attention. With the use of this technology, there have been progressed detection and visualization of a tissue underneath the retina (refer to (5) "Optical Coherence Tomography, by D. Huang, E. A. Swanson, C. P. Lin, J. S. Schuman, W. G. Chang, M. R. Hee, T. Flotted, K, Gregory, C. A. Puliafito and J. G. Fujimoto, Science, Vol., 254, pages 1,178 to 1,181; and (6): "Optical Coherency Microscopy in Scattering Media" by J. A. Izatt, M. R. Hee, G. M. Owen, E. A. Swanson and J. G. Fujimoto, Optics Letters, vol., 19, 1994, No. 8, pages 590 nto 592), measurement of an eye length ((7): "Eye-Length Measurement by Interferometry with Partially Coherent Light" by A. F. Frecher, K. Mengehot and W. Wrener, Optics Letters, Vol. 13, 1988, No. 3, pages 186 to 188, and (8); "Measurement of the Thickness of Fundus Layers by Partial Coherence tomography" by W. Drexier, C. K. Hltzenberger, H. Sattmann and A. F. Frecher, Optical Engineering, Vol. 34, 1955, No. 3, pages 701 to 710), and a basical experiment for precise detection of subcutaneous tissue ("Basical Experiment I for Precise Detection of Subcutaneous Tissue" by Shiraishi, Ohmi, Haruna and Nishihara, 56-th Scientific Lectured by Applied Physics Association. Autumn 1995, 26a-SN-11).

However, in the above-mentioned low coherence interferometry, collimated or focused beam is irradiated onto an object (a transparent plate) to be measured while the positions of two reference light mirrors are specified so that an optical path difference between reflecting signal beam and reference light from the front and rear surfaces of the object becomes zero, and an optical path length (group index ng×thickness t) between the front and rear surfaces of the object is measured from the spatial distance between the two mirrors. That is, since only the value of a group index×a thickness t) can be measured in this case, the group index or the phase index and the thickness t cannot separately be measured. It is noted here that the group index ng is dependent upon the FWHM of a light source, that is, the larger the FWHM, the larger the affection of wavelength dispersion, and accordingly, $\Delta n$ (=ng−np) becomes larger. It is noted that the refractive index n so-called in general is the phase index np.

The measurements of a phase index np (including a birefringence) and a thickness of a medium are indispensable factors for manufacturers who developing optical parts including lenses and optical materials. In particular, as to lenses, the measurement of a precise distribution of thickness is required together with a phase index np. Recently, in addition to optical parts made of various multi-component glass materials, optical parts made of polymers or liquid crystal, are widely used, the technology of and devices for simultaneously and precisely measuring a phase index np (including a birefringence) and a thickness of the material are indispensable for developing these parts. Further, the research and development for various nonlinear optical materials are prosperous at present, in order to use a short wave light source or a variable wavelength laser, and accordingly, the measurement of the refractive index (including a birefringence) of such a new optical material requires a convenient apparatus for simultaneously measuring a phase index np and a thickness t.

Further, in the medical field including the optical diagnosis and treatment field, the necessity of simultaneous measurements of a phase index and a thickness has been becoming hither and higher. For an example, ophthalmic diagnosis and treatment require precise measurements (with a high degree of precision which is about 10 $\mu$m) of an eye length, a thickness and a refractive index of the cornea. In this case, noncontact measurement is required as an indispensable condition, and accordingly, an optical probe is used. However, at present, since the refractive index ng and the thickness t cannot be measured separately from each other, the eye length, the thickness and the refractive index of the cornea cannot be precisely measured. Further, even with an optical CT (the optical build-up of optical biological tomographic images) which has been eagerly studied, simultaneous measurements of a refractive index np or ng and a thickness t are required.

Further, as to the quality evaluation and management of several kinds of protecting layers (films), evaluation using a refractive index as an evaluating index has bright prospects. This is directed to such a fact that the refractive indices of various kinds of hardenable resin vary due to shrinkage or the like as it is hardened. If a refractive index alone is measured, it can be made by using a usually used Abbe's refractomenter. However, such an Abbe's refractometer can measure a refractive index of a part only at a surface of an object to be measured, but cannot measure an averaged refractive index of an object to be measured, having a nonuniform distribution of refractive index in the thickness wise direction thereof (the surface of the object to be measured has been hardened but the interior thereof has been not yet, and so forth). This fact offers a serious barrier to evaluation of a hardened condition or a hardness of a resin, using refractive indices as evaluation indices. Further, a sample piece obtained from an object to be measured has to be made so as to satisfy terms required by an Abbe's refractometer, and a nondestructive measurement and a noncontact measurement cannot be carried out. In the case of using ultraviolet hardenable resin as an object to be measured, a hardening condition varies depending upon a thickness of the object to be measured, and accordingly, the value relating to the thickness of the object to be measured must be measured.

The present invention is devised in view of the above-mentioned circumstances, and accordingly, one object of the present invention is to provide a method of and an apparatus for measuring a medium, which can measure a phase index np, a birefringence and a thickness t of an object to be measured, separately from one another, and which uses an optical interferometry that can simultaneously measure both phase index np and group index ng, and to provide a method of evaluating and measuring a hardened condition or a hardness of hardenable resin with the use of a refractive index and with the use of the above-mentioned method and apparatus.

SUMMARY OF THE INVENTION

To the end, according to the present invention, there is provided a method of measuring a medium, using an optical interferometric system comprising a drive means for holding and mounting an object to be measured or a converging lens and a reference light mirror, a light source and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured or the converging lens and the reference light mirror are displaced so as to maximize the intensity of interference light caused by the reference light mirror and the front surface of the object to be measured and the intensity of interference light caused by the reference light mirror and the rear surface of the object to be measured, displaced distances of the object to be measured or the converging lens and the reference light mirror at a position where the intensity of interference light becomes maximum by the front surface and at a position where the intensity of interference light becomes maximum by the rear surface, are obtained whereby a refractive index and a thickness of the object to be measured are simultaneously measured.

Further, there is provided a method of measuring a medium using an optical interferometric system comprising a drive means for holding and mounting an object to be measured and a reference light mirror, a light source, a converging lens held by a holding means and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured and the reference light mirror are displaced so as to maximize the intensity of interference light caused by the reference light mirror and the front surface of the object to be measured and the intensity of interference light caused by the reference light mirror and the rear surface of the object to be measured, displaced distances of the object to be measured and the reference light mirror at a position where the intensity of interference light becomes maximum by the front surface and at a position where the intensity of interference light becomes maximum by the rear surface are obtained, whereby a refractive index and a thickness of the object to be measured are simultaneously measured.

Further, according to the present invention, there is provided a method of measuring a medium, using an optical interferometric system comprising a drive means for holding and mounting a converging lens and a reference light mirror, a light source, an object to be measured held by a holding means and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the converging lens and the reference light mirror are displaced so as to maximize the intensity of interference light caused by the reference light mirror and the front surface of the object to be measured and the intensity of interference light caused by the reference light mirror and the rear surface of the object to be measured, displaced distances of the converging lens and the reference light mirror at a position where the intensity of interference light becomes maximum by the front surface and at a position where the intensity of interference light becomes maximum by the rear surface are obtained, whereby a refractive index and a thickness of the object to be measured are simultaneously measured.

Further, according to the present invention, there is provided a method of measuring a medium, using an optical interferometric system comprising a drive means for holding and mounting an objective to be measured or a reference light mirror, a light source, and a light receiving element for synthesizing reflecting light from the object to be measured and reference light from the reference light mirror with each other causing interference so as to detect a light signal, characterized in that light from the light source of the optical interferometric system is irradiated to the object to be measured, the object to be measured or the reference light mirror is displaced so as to maximize an intensity of interference light caused by the reference mirror and the front surface of the object be measured and two intensities of interference lights caused by the reference light mirror and ordinary light rays and extraordinary rays from the rear surface of the object to be measured, a difference between displaced distances at a position where the intensity of interference light becomes maximum by the front surface and at a position where the intensities of interference light caused by the reference light mirror and the ordinary rays and the extraordinary rays become maximum caused by the rear surface, is obtained whereby a birefringence of the object to be measured are measured.

Further, according to the present invention, there is provided a method of measuring a medium, using an optical interferometric system comprising a drive means for holding and mounting an objective to be measured, a light source, a reference light mirror held by a holding means and a light receiving element for synthesizing reflecting light from the object to be measured and reference light from the reference light mirror with each other causing interference so as to detect a light signal, characterized in that light from the light source of the optical interferometric system is irradiated to the object to be measured, the object to be measured is displaced so as to maximize an intensity of interference light caused by the reference mirror and the front surface of the object be measured and two intensities of interference lights caused by the reference light mirror and ordinary light rays and extraordinary light rays from the rear surface of the object to be measured, a difference between displaced distances at a position where the intensity of interference light becomes maximum caused by the front surface and at a position where the two intensities of interference light caused by the reference light mirror and the ordinary rays and the extraordinary rays become maximum caused by the rear surface, are obtained whereby a birefringence of the object to be measured are measured.

Further, according to the present invention, there is provided a method of measuring a medium, using an optical interferometric system comprising a drive means for holding and mounting or a reference light mirror, a light source, an object to be measured held by a holding means and a light receiving element for synthesizing reflecting light from the object to be measured and reference light from the reference light mirror with each other causing interference so as to detect a light signal, characterized in that light from the light source of the optical interferometric system is irradiated to the object to be measured, the reference light mirror is displaced so as to maximize an intensity of interference light caused by the reference mirror and the front surface of the object be measured and two intensities of interference lights caused by the reference light mirror and ordinary light rays and extraordinary light rays from the rear surface of the object to be measured, a difference between displaced distances at a position where the intensity of interference light becomes maximum caused by the front surface and at a position where the two intensities of interference light caused by the reference light mirror and the ordinary rays and the extraordinary rays become maximum caused by the rear surface, is obtained whereby a birefringence of the object to be measured are measured.

Further, there is provided a method of measuring a medium, using an optical interferometric system comprising a drive means for holding and mounting an object to be measured or a converging lens and a reference light mirror, a light source and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured or the converging lens and the reference light mirror are displaced so as to maximize an intensity of interference light caused by the reference light mirror and the front surface of the object to be measured, and two intensities of interference light caused by the reference light mirror and ordinary light rays and extraordinary light rays from the rear surface of the object be measured, displaced distances of the object to be measured or the converging lens and the reference light mirror at a position where the intensity of interference light becomes maximum caused by the front surface and at a position where the two intensities of interference light become maximum caused by the rear surface, are obtained whereby a birefringence and a thickness of the object to be measured are simultaneously measured.

Further, there is provided a method of measuring a medium using an optical interferometric system comprising a drive means for holding and mounting an object to be measured and a reference light mirror, converging lens, a light source and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured and the reference light mirror are displaced so as to maximize an intensity of interference light caused by the reference light mirror and the front surface of the object to be measured and two intensities of interference light caused by the reference light mirror and ordinary light rays and extraordinary light rays from the rear surface of the object to be measured, displaced distances at a position where the intensity of interference light becomes maximum caused by the front surface and at a position where the two intensities caused by the reference light mirror and ordinary rays and extraordinary rays the ordinary rays and the extraordinary rays become maximum caused by the rear surface are obtained, whereby a birefreingence and and a thickness of the object to be measured are simultaneously measured.

Further, there is provided a method of measuring a medium using an optical interferometric system comprising a drive means for holding and mounting a converging lens and a reference light mirror, a light source, and an objective to be measured held by a holding means and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured and the reference light mirror are displaced so as to maximize an intensity of interference light caused by the reference light mirror and the front surface of the object to be measured and two intensities of interference light caused by the reference light mirror and ordinary light rays and extraordinary light rays from the rear surface of the object to be measured, displaced distances at a position where the intensity of interference light becomes maximum caused by the front surface and at a position where the two intensities caused by the reference light mirror and the ordinary rays and the extraordinary rays become maximum caused by the rear surface are obtained, whereby a birefringence and a thickness of the object to be measured are simultaneously measured.

Further, there is provided a method of measuring a medium, using an optical interferometric system comprising a drive means for holding and mounting an object to be measured or a converging lens and a reference light mirror, a light source and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured or the converging lens and the reference light mirror are displaced so as to maximize the intensity of interference light caused by the reference light mirror and the front surface of the object to be measured, and the intensity of interference light caused by the reference light mirror and the rear surface of the object to be measured, displaced distances of the object to be measured or the converging lens and the reference light mirror at a position where the intensity of interference light becomes maximum caused by the front surface and at a position where the intensity of interference light becomes maximum caused by the rear surface, are obtained whereby a phase index and a group index of the object to be measured are simultaneously measured.

Further, there is provided a method of measuring a medium, using an optical interferometric system comprising a drive means for holding and mounting an object to be measured and a reference light mirror, a light source, a converging lens held by a holding means and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured and the reference light mirror are displaced so as to maximize the intensity of interference light caused by the reference light mirror and the front surface of the object to be measured, and the intensity of interference light caused by the reference light mirror and the rear surface of the object to be measured, displaced distances of the object to be measured and the reference light mirror at a position where the intensity of interference light becomes maximum caused by the front surface and at a position where the intensity of interference light becomes maximum caused by the rear surface, are obtained whereby a phase index and a group index of the object to be measured are simultaneously measured.

Further, there is provided a method of measuring a medium, using an optical interferometric system comprising a drive means for holding and mounting a converging lens and a reference light mirror, a light source, an object to be measured held by a holding means and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the converging lens and the reference light mirror are displaced so as to maximize the intensity of interference light caused by the reference light mirror and the front surface of the object to be measured, and the intensity of interference light caused by the reference light mirror and the rear surface of the object to be measured, displaced distances of the converging lens and the reference light mirror at a position where the intensity of interference light becomes maximum caused by the front surface and at a position where the intensity of interference light becomes maximum caused by the rear surface, are obtained whereby a phase index and a group index of the object to be measured are simultaneously measured.

Further, there is provided an apparatus for measuring a medium characterized in that a refractive index and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the object to be measured or the converging lens and the reference light mirror and slightly moving them, and a light receiving element for synthesizing reflected light from the object to be measured and reference light from the reference light mirror for interference so as to detect a light signal.

Further, there is provided an apparatus for measuring a medium characterized in that a refractive index and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the object to be measured and the reference light mirror and slightly moving them, and a light receiving element for synthesizing reflected light from the object to be measured and reference light from the reference light mirror for interference so as to detect a light signal.

Further, there is provided an apparatus for measuring a medium characterized in that a refractive index and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, a means for holding and mounting the converging lens and the reference light mirror and slightly moving them, and a light receiving element for synthesizing reflected light from the object to be measured and reference light from the reference light mirror for interference so as to detect a light signal.

Further, there is provided an apparatus for measuring a medium characterized in that a birefringence of the medium is measured with the use of an interferometric system comprising a light source, a means for splitting light from the light source, a reference light mirror for receiving and reflecting one of light split by the splitting means, a means for irradiating an other one of light split by the splitting means, onto the object to be measured, a means for holding and mounting the object to be measured or the reference light mirror and slightly moving them, and a light receiving element for synthesizing reflected light from the object to be measured and reference light from the reference light mirror for interference so as to detect a light signal.

Further, there is provided an apparatus for measuring a medium characterized in that a birefringence of the medium is measured with the use of an interferometric system comprising a light source, a means for splitting light from the light source, a reference light mirror for receiving and reflecting one of light split by the splitting means, a means for irradiating the other one of light split by the splitting means, onto the object to be measured, through a converging lens, a means for holding and mounting the object to be measured and slightly moving it, and a light receiving element for synthesizing reflected light from the object to be measured and reference light from the reference light mirror for interference so as to detect a light signal.

Further, there is provided an apparatus for measuring a medium characterized in that a birefringence of the medium is measured with the use of an interferometric system comprising a light source, a means for splitting light from the light source, a reference light mirror for receiving and reflecting one of light split by the splitting means, a means for irradiating the other one of light split by the splitting means, onto an object to be measured, a means for holding and mounting the reference light mirror and slightly moving it, and a light receiving element for synthesizing reflected light from the object to be measured and reference light from the reference light mirror for interference so as to detect a light signal.

Further, there is provided an apparatus for measuring a medium characterized in that a birefringence and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the object to be measured or the converging lens and the reference light mirror and slightly moving them, and a light receiving element for synthesizing reflected light from the object to be measured and reference light from the reference light mirror for interference so as to detect a light signal.

Further, there is provided an apparatus for measuring a medium characterized in that a birefringence and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the object to be measured and the reference light mirror and slightly moving them, and a light receiving element for synthesizing reflected light from the object to be measured and reference light from the reference light mirror for interference so as to detect a light signal.

Further, there is provided an apparatus for measuring a medium characterized in that a birefringence and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the converging lens and the reference light mirror and slightly moving them, and a light receiving element for synthesizing reflected light from the object to be measured and reference light from the reference light mirror for interference so as to detect a light signal.

Further, there is provided an apparatus for measuring a medium characterized in that a phase index and a group index of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the object to be measured or the converging lens and the reference light mirror and slightly moving them, and a light receiving element for synthesizing reflected light from the object to be measured and reference light from the reference light mirror for interference so as to detect a light signal.

Further, there is provided an apparatus for measuring a medium characterized in that a phase index and a group index of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the object to be measured and the reference light mirror and slightly moving them, and a light receiving element for synthesizing reflected light from the object to be measured and reference light from the reference light mirror for interference so as to detect a light signal.

Further, there is provided an apparatus for measuring a medium characterized in that a phase index and a group index of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the converging lens and the reference light mirror and slightly moving them, and a light receiving element for synthesizing reflected light from the object to be measured and reference light from the reference light mirror for interference so as to detect a light signal.

According to one specific form of the present invention, the method or the apparatus for measuring a medium is characterized in that arithmetic formulae in consideration with a wavelength dispersion of the refractive index of the object to be measured, are used for the simultaneous measurement of the refractive index, and the birefringence and the thickness, so as to simultaneously derive the phase index and the thickness of the object to be measured.

Further, according to another specific form of the present invention, the method or the apparatus for measuring a medium is characterized in that the light source is the one for emitting low coherence light.

Further, according to another specific form of the present invention, the method of or the apparatus for measuring a medium is characterized in that the light source emitting the low coherence light is a linear polarization light source, a nonpolarization light source or a random polarization light source for simultaneously measuring the refractive index and the thickness, and the phase index and the group index.

Further, according to another specific form of the present invention, the method of or the apparatus for measuring a medium is characterized in that the light source is a nonpolarization light source or a random polarization light source for measuring the birefringence or simultaneously measuring the birefringence and the thickness.

Further, according to another specific form of the present invention, the method of or the apparatus for measuring a medium is characterized in that the light source for emitting the low coherent light has a coherence length $\Delta lc$ $(=((\ln(2))\times(2/\pi)\times(\lambda c^2/\Delta\lambda))/2)$ which is less than 30 $\mu$m.

Further, another specific form of the present invention, the method of or the apparatus for measuring a medium, characterized in that the light source for emitting the low coherent light is a light source in which light from a super luminescent diode or a white light source is subjected to spectroscopy for a specific wavelength range by a monochromator.

Further, another specific form of the present invention, the method of or the apparatus for measuring a medium is characterized by a means, one of components, for branching and synthesizing light from the light source.

Further, another specific form of the present invention, the method of and the apparatus for measuring a medium is characterized in that the means for holding and mounting the object to be measured, the converging lens or the reference light mirror is a slight motion stage.

Further, another specific form of the present invention, the method of or the apparatus for measuring a medium is characterized in that the reference light mirror is secured to a vibrator for vibrating the reference mirror in order to phase-modulate the reference light in the optical interferometric system.

Further, another specific form of the present invention, the method of or the apparatus for measuring a medium, is characterized in that the phase-modulation of the reference light is made by applying vibration having an amplitude which is less than $\lambda c/2$ where $\lambda c$ is the oscillating center wavelength of the light source, and having a frequency of higher than 100 Hz.

Further, another specific form of the present invention, the method of or the apparatus for measuring a medium, is characterized in that the light receiving element is a photodiode for heterodyne detection.

Further, another specific form of the present invention, the method of or the apparatus for measuring a medium, is characterized in that, a detection signal subjected to the heterodyne detection is converted into a digital signal by a detecting circuit.

Further, another specific form of the present invention, the method of or the apparatus for measuring a medium, is characterized in that the object to be measured is a medium which does not completely absorb light from the light source.

Further, another specific form of the present invention, the method of or the apparatus for measuring a medium, is characterized in that the object to be measured is a biological tissue.

Further, there is provided a method of measuring a medium characterized in that a hardened condition or a degree of hardness of hardenable resin is evaluated with the use of a refractive index which is averaged in the thickness-wise direction of the hardenable resin, as an evaluation index.

Further, there is provided a method of measuring a refractive index of a hardenable resin using an optical interferometric system comprising a drive means for holding and mounting an object to be measured or a converging lens and a reference light mirror, a light source and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured or the converging lens and the reference light mirror are displaced so as to maximize the intensity of interference light caused by the reference light mirror and the front surface of the object to be measured, and the intensity of interference light caused by the reference light mirror and the rear surface of the object to be measured, displaced distances of the object to be measured or the converging lens and the reference light mirror at a position where the intensity of interference light becomes maximum caused by the front surface and at a position where the intensity of interference light becomes maximum caused by the rear surface, are obtained whereby a refractive index and a thickness of the object to be measured are simultaneously measured.

Further, there is provided a method of measuring a refractive index of hardenable resin using an optical interferometric system comprising a drive means for holding and mounting an object to be measured and a reference light mirror, a light source, a converging lens held by a holding means and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured and the reference light mirror are displaced so as to maximize the intensity of interference light caused by the reference light mirror and the front surface of the object to be measured, and the intensity of interference light caused by the reference light mirror and the rear surface of the object to be measured, displaced distances of the object to be measured and the reference light mirror at a position where the intensity of interference light becomes maximum caused by the front surface and caused by a position where the intensity of interference light becomes maximum at the rear surface are obtained, whereby a refractive index and a thickness of the object to be measured are simultaneously measured.

Further, there is provided a method of measuring a refractive index of hardenable resin, using an optical interferometric system comprising a drive means for holding and mounting a converging lens and a reference light mirror, a light source an object to be measured held by a holding means and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the converging lens and the reference light mirror are displaced so as to maximize the intensity of interference light caused by the reference light mirror and the front surface of the object to be measured, and the intensity of interference light caused by the reference light mirror and the rear surface of the object to be measured, displaced distances of the converging lens and the reference light mirror at a position where the intensity of interference light becomes maximum caused by the front surface and at a position where the intensity of interference light becomes maximum caused by the rear surface, are obtained whereby a refractive index and a thickness of the object to be measured are simultaneously measured.

Further, according to the present invention, there is provided apparatus for measuring a refractive index of hadenable resin is characterized in that a refractive index and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means onto an object to be measured, through the converging lens, a means for holding and mounting the object to be measured or the converging lens and the reference light mirror and slightly moving them, and a light receiving element for synthesizing reflected light from the object to be measured and reference light from the reference light mirror for interference so as to detect a light signal.

Further, according to the present invention, there is provided an apparatus for measuring a refractive index of hardenable resin characterized in that a refractive index and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through the converging lens, a means for holding and mounting the object to be measured and the reference light mirror and slightly moving them, and a light receiving element for synthesizing reflected light from the object to be measured and reference light from the reference light mirror for interference so as to detect a light signal.

Further, according to the present invention, there is provided an apparatus for measuring a refractive index of hardenable resin characterized in that a refractive index and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through the converging lens, a means for holding and mounting the converging lens and the reference light mirror and slightly moving them, and a light receiving element for synthesizing reflected light from the object to be measured and reference light from the reference light mirror for interference so as to detect a light signal.

BRIEF DESCRIPTION OF THE DRAWINGS

FIGS. 13a to 13d are views for explaining a process for displacing a sample to be measured, and a process for displacing a reference light mirror in the birefringence measuring method in an embodiment of the present invention;

DETAILED DESCRIPTION OF THE INVENTION

Figure 1:
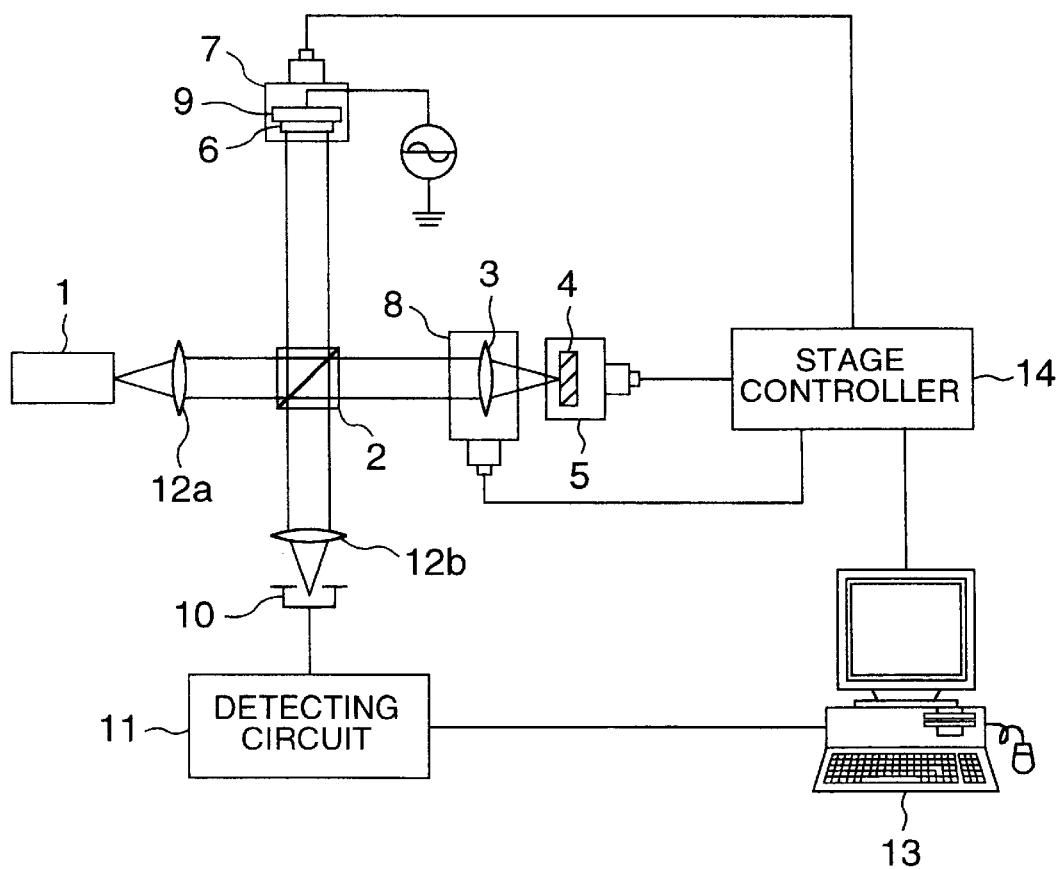
FIG. 1 is a block diagram illustrating a basic system for simultaneously measuring a phase index and a thickness, and a phase index and a group index in an embodiment of the present invention.

According to the present invention, there is provided a method of measuring a medium, using an optical interferometric system comprising a drive means for holding and mounting an object to be measured or a converging lens and a reference light mirror, a light source and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured or the converging lens and the reference light mirror are displaced so as to maximize the intensity of interference light caused by the reference light mirror and the front surface of the object to be measured, and the intensity of interference light caused by the reference light mirror and the rear surface of the object to be measured, displaced distances of the object to be measured or the converging lens and the reference light mirror caused by a position where the intensity of interference light becomes maximum caused by the front surface and at a position where the intensity of interference light becomes maximum caused by the rear surface, are obtained whereby a refractive index and a thickness of the object to be measured are simultaneously measured. With this arrangement, a refractive index and a thickness of an object to be measured, can be measured separately and simultaneously measured in a noncontact manner.

Further, according to the present invention, there is provided a method of measuring a medium using an optical interferometric system comprising a drive means for holding and mounting an object to be measured and a reference light mirror, a light source, a converging lens held be a holding means and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured and the reference light mirror are displaced so as to maximize the intensity of interference light caused by the reference light mirror and the front surface of the object to be measured, and the intensity of interference light caused by the reference light mirror and the rear surface of the object to be measured, displaced distances of the object to be measured and the reference light mirror at a position where the intensity of interference light becomes maximum at the front surface and at a position where the intensity of interference light becomes maximum caused by the rear surface are obtained, whereby a refractive index and a thickness of the object to be measured are simultaneously measured. With this arrangement, a refractive index and a thickness of an object to be measured, can be measured separately and simultaneously measured in a noncontact manner by displacing the object to be measured and the reference light mirror.

Further, according to the present invention, there is provided a method of measuring a medium, using an optical interferometric system comprising a drive means for holding and mounting a converging lens and a reference light mirror, a light source, an object to be measured held by a holding means and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the converging lens and the reference light mirror are displaced so as to maximize the intensity of interference light caused by the reference light mirror and the front surface of the object to be measured, and the intensity of interference light caused by the reference light mirror and the rear surface of the object to be measured, displaced distances of the converging lens and the reference light mirror at a position where the intensity of interference light becomes maximum caused by the front surface and at a position where the intensity of interference light becomes maximum caused by the rear surface are provided, whereby a refractive index and a thickness of the object to be measured are simultaneously measured. With this arrangement, a refractive index and a thickness of an object to be measured, can be measured separately and simultaneously measured in a noncontact manner by displacing the converging lens and the reference light mirror while making the object to be measured stationary.

Further, according to the present invention, there is provided a method of measuring a medium, using an optical interferometric system comprising a drive means for holding and mounting an objective to be measured or a reference light mirror, a light source, and light receiving element for synthesizing reflecting light from the object to be measured and reference light from the reference light mirror with each other causing interference so as to detect a light signal, characterized in that light from the light source of the optical interferometric system is irradiated to the object to be measured, the object to be measured or the reference light mirror is displaced so as to maximize an intensity of interference light caused by the reference mirror and the front surface of the object be measured and two intensities of interference lights caused by the reference light mirror and ordinary light rays and extraordinary light rays from the rear surface of the object to be measured, a difference between displaced distances at a position where the intensity of interference light becomes maximum caused by the front surface and at a position where the intensities of interference light caused by the reference light mirror and the ordinary rays and the extraordinary rays become maximum caused by the rear surface, is obtained whereby a birefringence of the object to be measured are measured. With this arrangement, a birefingence of an object to be measured, can be measured in a noncontact manner with a very simple structure.

Further, according to the present invention, there is provided a method of measuring a medium, using an optical interferometric system comprising a drive means for holding and mounting an objective to be measured, a light source, a reference light mirror held by a holding means and a light receiving element for synthesizing reflecting light from the object to be measured and reference light from the reference light mirror with each other causing interference so as to detect a light signal, characterized in that light from the light source of the optical interferometric system is irradiated to the object to be measured, the object to be measured is displaced so as to maximize an intensity of interference light caused by the reference mirror and the front surface of the object be measured and two intensities of interference lights caused by the reference light mirror and ordinary light rays and extraordinary light rays from the rear surface of the object to be measured, a difference between displaced distances at a position where the intensity of interference light becomes maximum caused by the front surface and at a position where the two intensities of interference light caused by the reference light mirror and the ordinary rays and the extraordinary rays become maximum caused by the rear surface, are obtained whereby a birefringence of the object to be measured are measured. With this arrangement, the birefringence can be conveniently measured only by displacing the object to be measured.

Further, according to the present invention, there is provided a method of measuring a medium, using an optical interferometric system comprising a drive means for holding and mounting or a reference light mirror, a light source, an object to be measured held by a holding means and a light receiving element for synthesizing reflecting light from the object to be measured and reference light from the reference light mirror with each other causing interference so as to detect a light signal, characterized in that light from the light source of the optical interferometric system is irradiated to the object to be measured, the reference light mirror is displaced so as to maximize an intensity of interference light caused by the reference mirror and the front surface of the object be measured and two intensities of interference lights caused by the reference light mirror and ordinary light rays and extraordinary light rays from the rear surface of the object to be measured, a difference between displaced distances at a position where the intensity of interference light becomes maximum caused by the front surface and at a position where the two intensities of interference light caused by the reference light mirror and the ordinary rays and the extraordinary rays become maximum caused by the rear surface, is obtained whereby a birefringence of the object to be measured are measured. With this arrangement, the birefringence can be conveniently measured by displacing only the mirror light mirror while the object to be measured is fixed.

Further, there is provided a method of measuring a medium, using an optical interferometric system comprising a drive means for holding and mounting an object to be measured or a converging lens and a reference light mirror, a light source and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured or the converging lens and the reference light mirror are displaced so as to maximize an intensity of interference light caused by the reference light mirror and caused by the front surface of the object to be measured, and two intensities of interference light caused by the reference light mirror and ordinary light rays and extraordinary light rays from of the object to be measured, displaced distances of the object to be measured or the converging lens and the reference light mirror at a position where the intensity of interference light becomes maximum caused by the front surface and at a position where the two intensities of interference light become maximum caused by the rear surface, are obtained whereby a birefringence and a thickness of the object to be measured are simultaneously measured. With this arrangement, the birefringence and the thickness of the object to be measured can be separately and simultaneously measured in a noncontact manner.

Further, according to the present invention, there is provided a method of measuring a medium using an optical interferometric system comprising a drive means for holding and mounting an object to be measured and a reference light mirror, a converging lens, a light source and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured and the reference light mirror are displaced so as to maximize an intensity of interference light caused by the reference light mirror and the front surface of the object to be measured and two intensities of interference light caused by the reference light mirror and ordinary light rays and extraordinary light rays from the rear surface of the object to be measured, a difference between displaced distances at a position where the intensity of interference light becomes maximum caused by the front surface and at a position where the two intensities caused by the reference light mirror and the ordinary rays and the extraordinary rays become maximum caused by the rear surface is obtained, whereby a birefrengence and a thickness of the object to be measured are simultaneously measured. With this arrangement, the birefringence and the thickness of the object to be measured can be conveniently, separately and simultaneously measured in a noncontact manner by displacing only the object to be measured and the reference light mirror.

Further, according to the present invention, there is provided a method of measuring a medium using an optical interferometric system comprising a drive means for holding and mounting a converging lens and a reference light mirror, a light source, and an objective to be measured held by a holding means and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured and the reference light mirror are displaced so as to maximize an intensity of interference light caused by the reference light mirror and the front surface of the object to be measured and two intensities of interference light caused by the reference light mirror and ordinary light rays and extraordinary light rays from the rear surface of the object to be measured, a difference between displaced distances at a position where the intensity of interference light becomes maximum caused by the front surface and at a position where the two intensities caused by the reference light mirror and the ordinary rays and the extraordinary rays become maximum caused by the rear surface is obtained, whereby a birefrengence and a thickness of the object to be measured are simultaneously measured. With this arrangement, the birefringence and the thickness of the object to be measured can be conveniently, separately and simultaneously measured in a noncontact manner by displacing only the converging lend and the reference light mirror.

Further, according to the present invention, there is provided a method of measuring a medium, using an optical interferometric system comprising a drive means for holding and mounting an object to be measured or a converging lens and a reference light mirror, a light source and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured or the converging lens and the reference light mirror are displaced so as to maximize the intensity of interference light caused by the reference light mirror and the front surface of the object to be measured, and the intensity of interference light caused by the reference light mirror and the rear surface of the object to be measured, displaced distances of the object to be measured or the converging lens and the reference light mirror at a position where the intensity of interference light becomes maximum caused by the front surface and at a position where the intensity of interference light becomes maximum caused by the rear surface, are obtained whereby a phase index and a group index of the object to be measured are simultaneously measured. With this arrangement, the phase index and the group index of the object to be measured having a known thickness, can be simultaneously be measured in a noncontact manner, Further, according to the present invention, there is provided a method of measuring a medium, using an optical interferometric system comprising a drive means for holding and mounting an object to be measured and a reference light mirror, a light source, a converging lens held by a holding means and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the object to be measured and the reference light mirror are displaced so as to maximize the intensity of interference light caused by the reference light mirror and the front surface of the object to be measured, and the intensity of interference light caused by the reference light mirror and the rear surface of the object to be measured, displaced distances of the object to be measured and the reference light mirror at a position where the intensity of interference light becomes maximum caused by the front surface and at a position where the intensity of interference light becomes maximum caused by the rear surface, are obtained whereby a phase index and a group index of the object to be measured are simultaneously measured. With this arrangement, the birefringence and the group index of the object to be measured can be separately and simultaneously measured in a noncontact manner by displacing only the object to be measured and the reference light mirror by displacing the object to be measured and the reference light mirror.

Further, there is provided a method of measuring a medium, using an optical interferometric system comprising a drive means for holding and mounting a converging lens and a reference light mirror, a light source, an object to be measured held by a holding means and a light receiving element for synthesizing reflecting light from the object to be measured and reference light from the reference light mirror with each other causing interference so as to detect a light signal, characterized in that light from the light source of the optical interferometric system is converged by the converging lens and is irradiated to the object to be measured, the converging lens and the reference light mirror are displaced so as to maximize the intensity of interference light caused by the reference light mirror and the front surface of the object to be measured, and the intensity of interference light caused by the reference light mirror and the rear surface of the object to be measured, displaced distances of the converging lens and the reference light mirror at a position where the intensity of interference light becomes maximum caused by the front surface and at a position where the intensity of interference light becomes maximum caused by the rear surface, are obtained whereby the phase index and the group index can simultaneously be measured. With this arrangement, the phase index and the group index can be simultaneously measured having a known thickness by displacing the converging lend and the reference light mirror while making the object to be measured stationary.

Further, according to the present invention, there is provided an apparatus for measuring a medium characterized in that a refractive index and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the object to be measured or the converging lens and the reference light mirror and slightly moving them, and a light receiving element for synthesizing reflected light from the object to be measured and reference light from the reference light mirror for interference so as to detect a light signal. With this arrangement, the refractive index and the thickness of the object to be measured can be simultaneously measured only by adding the drive means for holding and mounting the object to be measured or the converging lens and the reference light mirror and for slightly moving them in the simple interferometric system.

Further, according to the present invention, there is provided an apparatus for measuring a medium characterized in that a refractive index and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the object to be measured and the reference light mirror and slightly moving them, and a light receiving element for synthesizing reflected light from the object to be measured and reference light from the reference light mirror for interference so as to detect a light signal. With this arrangement, the refractive index and the thickness of the object to be measured can be simultaneously measured only by adding the drive means for holding and mounting the object to be measured and the reference light mirror and for slightly moving them in the simple interferometric system.

Further, according to the present invention, there is provided an apparatus for measuring a medium characterized in that a refractive index and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the converging lens and the reference light mirror and slightly moving them, and a light receiving element for synthesizing reflected light from the object to be measured and reference light from the reference light mirror for interference so as to detect a light signal. With this arrangement, the refractive index and the thickness of the object to be measured can be simultaneously measured only by adding the drive means for holding and mounting the converging lens and the reference light mirror and for slightly moving them in the simple interferometric system while making the object to be measured stationary.

Further, according to the present invention, there is provided an apparatus for measuring a medium characterized in that a birefringence of the medium is measured with the use of an interferometric system comprising a light source, a means for splitting light from the light source, a reference light mirror for receiving and reflecting one of light split by the splitting means, a means for irradiating an other one of light split by the splitting means, onto the object to be measured, a means for holding and mounting the converging lens or the reference light mirror and slightly moving them, and a light receiving element for synthesizing reflected light from the object to be measured and reference light from the reference light mirror for interference so as to detect a light signal. With this arrangement, the birefringence of the object to be measured can be measured only by adding the drive means for holding and mounting the object to be measured or the reference light mirror and slightly displacing it in the simple optical interferometric system.

Further, according to the present invention, there is provided an apparatus for measuring a medium characterized in that a birefringence of the medium is measured with the use of an interferometric system comprising a light source, a means for splitting light from the light source, a reference light mirror for receiving and reflecting one of light split by the splitting means, a means for irradiating the other one of light split by the splitting means, onto the object to be measured, a means for holding and mounting the object to be measured and slightly moving it, and a light receiving element for synthesizing reflected light from the object to be measured and reference light from the reference light mirror for interference so as to detect a light signal. With this arrangement, the birefringence of the object to be measured can be measured only by adding the drive means for holding and mounting the object to be measured and slightly displacing it in the simple optical interferometric system.

Further, there is provided an apparatus for measuring a medium characterized in that a birefringence of the medium is measured with the use of an interferometric system comprising a light source, a means for splitting light from the light source, a reference light mirror for receiving and reflecting one of light split by the splitting means, a means for irradiating the other one of light split by the splitting means, onto an object to be measured, a means for holding and mounting the reference light mirror and slightly moving it, and a light receiving element for synthesizing reflected light from the object to be measured and reference light from the reference light mirror for interference so as to detect a light signal. With this arrangement, the birefringence of the object to be measured can be measured only by adding the drive means for holding and mounting the reference light mirror and lightly displacing it in the simple optical interferometric system.

Further, there is provided an apparatus for measuring a medium characterized in that a birefringence and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the object to be measured or the converging lens and the reference light mirror and slightly moving them, and a light receiving element for synthesizing reflected light from the object to be measured and reference light from the reference light mirror for interference so as to detect a light signal. With this arrangement, the birefringence and the thickness of the object to be measured can be simultaneously measured only by adding the drive means for holding and mounting the object to be measured or the converging lens and the reference light mirror and slightly displacing them in the simple optical interferometric system.

Further, according to the present invention, there is provided an apparatus for measuring a medium characterized in that a birefringence and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the object to be measured and the reference light mirror and slightly moving them, and a light receiving element for synthesizing reflected light from the object to be measured and reference light from the reference light mirror for interference so as to detect a light signal. With this arrangement, the birefringence and the thickness of the object to be measured can simultaneously be measured only by adding the drive means for holding and mounting the object to be measured and the reference light beam and slightly displacing them in the simple optical interferometric system.

Further, according to the present invention, there is provided an apparatus for measuring a medium characterized in that a birefringence and a thickness of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the converging lens and the reference light mirror and slightly moving them, and a light receiving element for synthesizing reflected light from the object to be measured and reference light from the reference light mirror for interference so as to detect a light signal. With this arrangement, the birefringence and the thickness of the object to be measured can simultaneously be measured only by adding the drive means for holding and mounting the converging lens and the reference light mirror and slightly displacing them in the simple optical interferometric system while making the object to be measured stationary.

Further, according to the present invention, there is provided an apparatus for measuring a medium characterized in that a phase index and a group index of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto an object to be measured, through a converging lens, a means for holding and mounting the object to be measured or the converging lens and the reference light mirror and slightly moving them, and a light receiving element for synthesizing reflected light from the object to be measured and reference light from the reference light mirror for interference so as to detect a light signal. With this arrangement, the phase index and the group index of the object to be measured having a known thickness can simultaneously be measured only by adding the drive means for holding and mounting the object to be measured or the converging lens and the reference light mirror and slightly displacing them in the simple optical interferometric system.

Further, according to the present invention, there is provided an apparatus for measuring a medium characterized in that a phase index and a group index of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto the object to be measured, through a converging lens, a means for holding and mounting the object to be measured and the reference light mirror and slightly moving them, and a light receiving element for synthesizing reflected light from the object to be measured and reference light from the reference light mirror for interference so as to detect a light signal. With this arrangement, the phase index and the group index of the object to be measured having a known thickness can simultaneously be measured only by adding the drive means for holding and mounting the object to be measured and the reference light mirror and slightly displacing them in the simple optical interferometric system.

Further, according to the present invention, there is provided an apparatus for measuring a medium characterized in that a phase index and a group index of the medium are simultaneously measured with the use of an interferometric system comprising a light source, a means for splitting light from the light source, a reference light mirror for receiving and reflecting one of light split by the splitting means, a means for irradiating the other one of light split by the splitting means, onto the object to be measured, through a converging lens, a means for holding and mounting the converging lens and the reference light mirror and slightly moving them, and a light receiving element for synthesizing reflected light from the object to be measured and reference light from the reference light mirror for interference so as to detect a light signal. With this arrangement, the phase index and the group index of the object to be measured having a know thickness can simultaneously be measured only by adding the drive means for holding and mounting the object to be measured or the converging lens and the reference light mirror and slightly displacing them in the simple optical interferometric system while making the object to be measured stationary.

According to the present invention, there is provided a method of measuring a medium characterized by measuring a refractive index of the hardenable resin, which is average in the thicknesswise direction of the hardenable resin so as to evaluate a hardened condition of a hardness of hadenable resin with the use of the averaged refractive index as an evaluation index.

It is noted that a low coherence light source should not only limited to a super luminescent diode or a white light source but also all of light sources having a coherence length of less than 30 $\mu$m such as a laser diode which can be driven by an inrush current less than its threshold value, can be used. Accordingly, in the method and the apparatus according to the present invention, by using a plurality of laser diode having different oscillating center wavelengths or the like together, as similar to using a light source in which a white light source is subjected to spectroscopy by a monochromator, the wavelength dispersion of the refractive index of an object to be measured can be measured. Further, as to the components of the optical interferometric system, those which can branch light from a light source, and can synthesize signal light and reference light for interference, such as a beam splitter, a half-miller, a single mode fiber coupler and the like can be used. Further, the drive means should not be limited to a slight motion stage, but any of those which can precisely measure its displacement, Further, as to the vibrator, a piezoelectric actuator, an electromagnetic actuator or the like which can stably offer vibration and amplitude can be used.

Explanation will be hereinbelow made of simultaneous measurement of a phase index np or a birefringence and a thickness t of an object to be measured, measurement of a birefringence, a simultaneous measurement principle of a phase index and a group index, and evaluation of a hardened condition or a hardness of hardenable resin in consideration with a refractive index.

FIG. 1 is a block diagram which shows a basic system in an embodiment of the present invention, for the simultaneous measurement of a phase index and a thickness, the simultaneous measurement of a birefringence and a thickness, the measurement of a birefringence, and the simultaneous measurement of a phase index and a group index. First, the optical pathway of the basic system will be explained. Light emitted from a light source 1 is turned into a collimated beam by a lens 12a and is led into a light branching and synthesizing means for branching and synthesizing the light from the light source 1. The light is therefore equally divided into two branch beams one of which advances straightfoward so as to be converged by a converging lens 3 held and mounted on a drive means 8, and is irradiated onto an object 4 to be measured which is held and mounted on a drive means 5. On the contrary, the other one of the branching beams advances at a right angle from the branching and synthesizing means 2 and is irradiated onto a reference light mirror 6 which is held and mounted to a drive means 7 and is fixed to a vibrator 9 which is applied thereto with vibration having a frequency f and a predetermined amplitude so as to phase-modulate a reflected beam (reference beam) from the reference light mirror 6. A reflected beam (signal beam) from the object 4 to be measured, is led to a light receiving element 10 through the converging lens 3, the branching and synthesizing means 2 and a lens 12b. Further, the reflected beam (reference beam) from the reference light mirror 6 is led to the light receiving element 11 through the branching and synthesizing means 6 and the lens 12b. A detection signal from the light receiving element 10 is converted into a digital signal by a detection circuit 11, which is processed by a PC 11. It is noted that drive means 5, 7, 8 are controlled in accordance with a signal from the PC 13 through a stage controller 14.

As to the method of simultaneously measuring a phase index np or a birefringence and a thickness t of an object to be measured, and the method of simultaneously measuring a phase index np and a group index gp, there are two methods, that is, a method in which the converging lens 3 is made to be stationary, and the object 4 to be measured and the reference light mirror 6 are displaced in the direction of the optical axis, and a method in which the object 4 to be measured is made to be stationary, and the converging lens 3 and the reference light mirror 5 are displaced in the direction of the optical axis. These two methods will be hereinbelow explained.

1)-1 Process of Displacing Sample to be Measured

A process of displacing a sample to be measured will be explained with reference to FIGS. 1, 2a to 2d, 3a to 3d, 4, 6, 7 and 10.

Figure 2A:
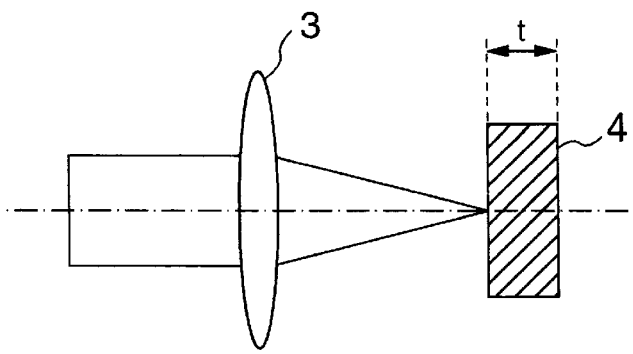
FIGS. 2a to 2d are views for explaining a process for displacing a sample to be measured and a process for displacing a lens, in an embodiment of the present invention.
Figure 3A:
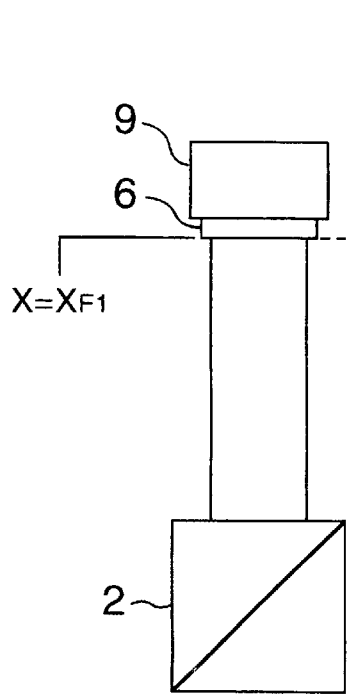
FIGS. 3a to 3d are views for explaining a process for displacing a converging lens and a process for displacing a reference light mirror, in an embodiment of the present invention.
Figure 6A:
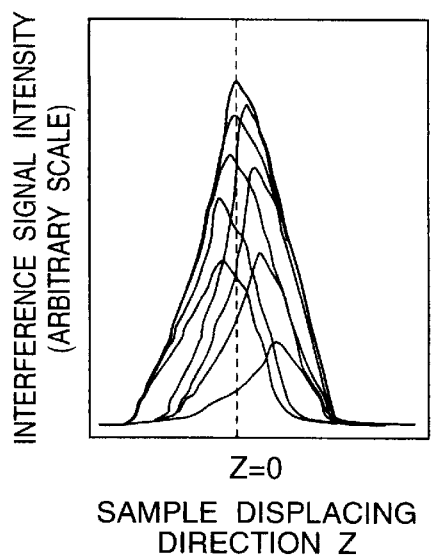
FIGS. 6a and 6b are graphs showing a reference intensities at from and rear surface, which are measured by the sample displacing process in an embodiment of the present invention.

In this sample displacing process, as shown in FIG. 2a, light from the light source 1 is converged onto the front surface of the object 4 to be measured, and then, as shown in FIG. 3a, the position of the reference light mirror 6 is adjusted by the drive means 7 so as to set the difference between the optical path lengths of the reference light beam and the signal light arm to zero. As shown in FIG. 3a, the position of the reference light mirror 6 is adjusted by the drive means 7. FIG. 6 shows intensity patterns of interference signals which are obtained when the position of the reference light mirror 6 is displaced at predetermined intervals while the object 4 to be measured is displaced by the drive means 5 after the light beam from the converging lens 3 is focused at a position in the vicinity of the object 4 to be measured. From the position where the intensity of the interference signal becomes maximum, z=0 is determined, and the position of the reference light mirror 6 corresponding thereto is $x=x_{F1}$.

Figure 2B:
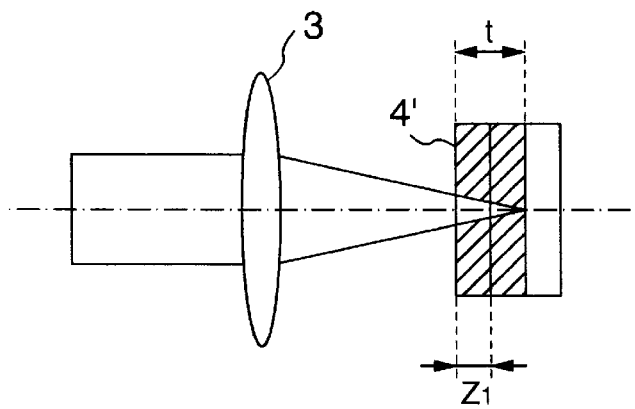
Figure 3B:
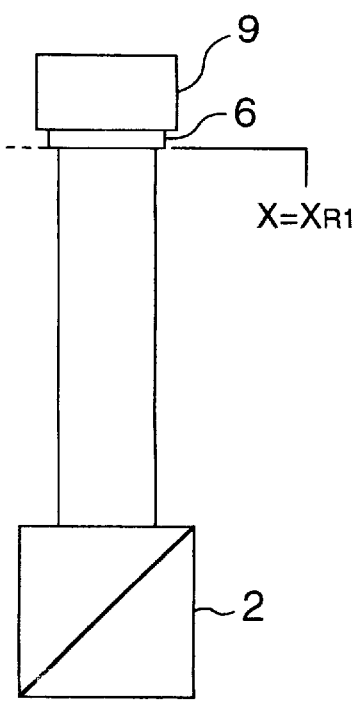
Figure 6B:
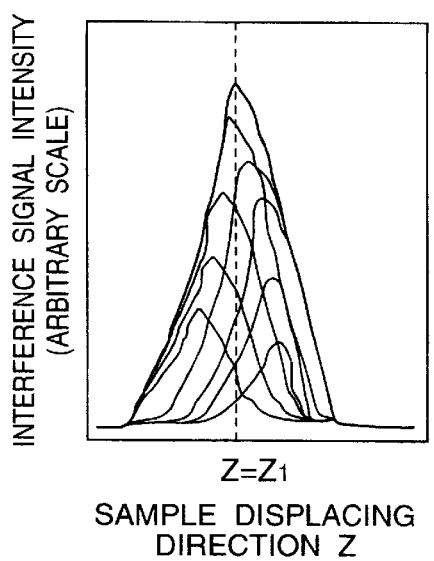
Figure 7:
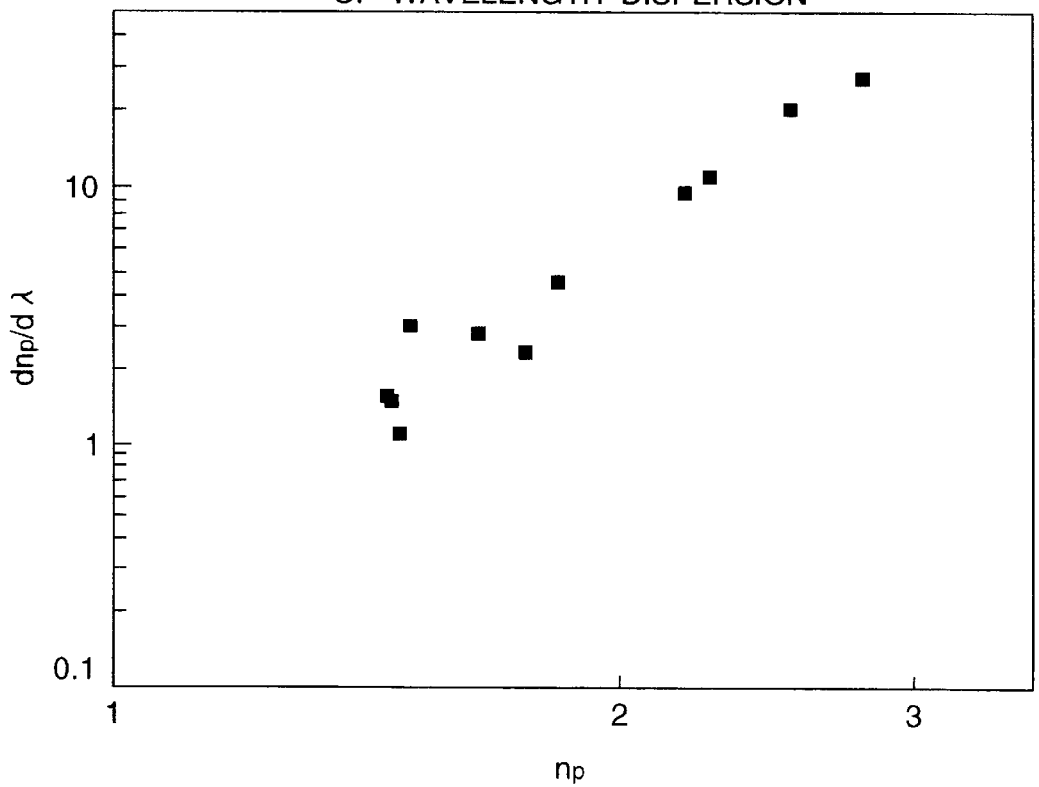
FIG. 7 is a graph showing examples of relationships between wavelength dispersion and phase index of various kinds of objects to be measured in an embodiment of the present invention.

Next, as shown in FIG. 2(b), the drive means 5 is moved so as to cause the object 4 to be measured, to approach the converging lens 3 so that the light beam is focused onto the rear surface of the object to be measured. Then, as shown in FIG. 3b, the reference mirror is moved by $\Delta L_1$ by the drive means 7 so that an optical path difference between two arms of an interferometer becomes again zero. FIG. 6b shows intensity patterns of interference signals which are obtained when the position of the reference light mirror 6 is displaced at predetermined intervals while the object 4 to be measured is displaced by the drive means 5 after the light beam from the converging lens 3 is focused in the vicinity of the rear surface of the object 4 to be measured, From a position where the intensity of the interference signal becomes maximum, $z=z_1$ is determined, and the position of the reference light mirror 6 (drive means 7) corresponding thereto is $x=x_{R1}$.

Figure 4:
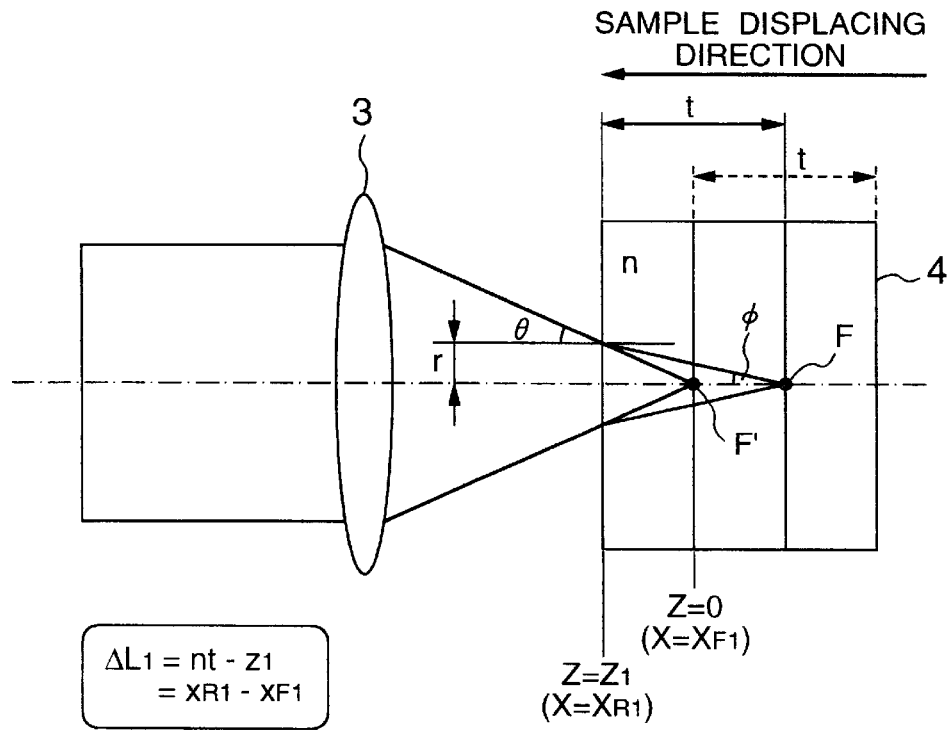
FIG. 4 is a view for explaining a principle of the sample displacing process in an embodiment of the present invention.

As shown in FIG. 4, first such a condition F' that the light beam is focused to the front surface of the object 4 to be measured (indicated by the thin line in the figure), is used as a reference, the object 4 to be measured (drive means 5) is displaced to the converging lens 3 by the distance of $z_1$, and the light beam is focused to the rear surface thereof. In this case F (indicated by the solid line in the figure), from the Snell's law, the following formula is given;

$$\sin\theta = n \times \sin\phi \qquad \text{EQ1}$$

-continued $$z_1 = t \times \frac{r}{\tan\theta} = t \times \frac{\tan\phi}{\tan\theta}$$

where θ is an incident angle to the object to be measured, r is an incident position and φ is a refracting angle.

From EQ1, $$z_1 = t \times \sqrt{\frac{1 - \sin^2\theta}{n^2 - \sin^2\theta}} \qquad \text{EQ2}$$

is obtained.

At this stage, the displaced distance $\Delta L_1$ of the above-mentioned reference light mirror 6 (drive means 7) is obtained. $\Delta L_1$ is a optical path difference between the case where the light beam is focused to the front surface (z=0 plane) of the object 4 to be measured (indicated by the thin line in the figure) and the case where the object 4 to be measured (drive means 5) is displaced by $z_1$ and focused to the rear surface (indicated by the solid line in the figure), and is equal to the optical path difference between two focus points F, F' with respect to $z=z_1$ as a reference. The phase of the convergent light beam (or the divergent light beam) after passing the converging lens, can be considered as being represented by a light ray passing through the center axis of the converging lens 3, and accordingly, $$\Delta L_1 = n \times t - z_1 \qquad \text{EQ3}$$

At this stage, since the object 4 to be measured (drive means 5) is displaced, it should be noted that the optical path length $\Delta L_1$ varies depending upon the displaced distance $z_1$. From EQ2 and EQ3, t is eliminated, and then $$n^2 = \frac{1}{2}\left\{\sin^2\theta + \sqrt{\sin^4\theta + 4(1 - \sin^2\theta) \times \left(1 + \frac{\Delta L_1}{z_1}\right)^2}\right\} \qquad \text{EQ4}$$

is obtained.

From EQ4, it is understood that if the aperture number NA (=sin θ) of the converging lens 3 is known, the refractive index n of the object 4 to be measured can be obtained from the ratio between the measured value $\Delta L_1(1)$ and the displaced distance $z_1$. Further, the thickness t thereof can be obtained from EQ3, and is given by $$t = \frac{\Delta L_1 + z_1}{n} \qquad \text{EQ5}$$

That is, referring to FIG. 4, the light beam is converged to the front surface of the object 4 to be measured (the position z=0 of the drive means 5: focus point F'), and then the position where a maximum intensity of an interference signal can be obtained (the position $x=x_{F1}$ of the drive mean 7) of the reference light mirror 6 is detected and digitalized by the detecting circuit 11, and is delivered to the PC 13, and further, the object 4 to be measured is displaced toward the converging lens 3 by the distance $z_1$ so as to obtain data. Thus, $x_{F1}$ which gives a maximum optical interference intensity is specified. Then the object 4 to be measured is moved toward the converging lens 3 by the distance $z_1$ (focusing at the rear surface of the object 4 to be measured, $z=z_1$: focus point F), and in this condition, the drive means 7 is adjusted so as to cause the interference signal intensity to be again maximum in order to specify the position thereof $x=x_{R1}$, similar to the above-mentioned $x_{F1}$. The optical path difference between two conditions in which focusing is made at the front and rear surfaces is given by $\Delta L_1 = x_{R1} - x_{F1}$, and accordingly, from these two independent values $\Delta L_1$, $z_1$, the refractive index n and the thickness t of the object 4 to be measured can be obtained.

Figure 10:
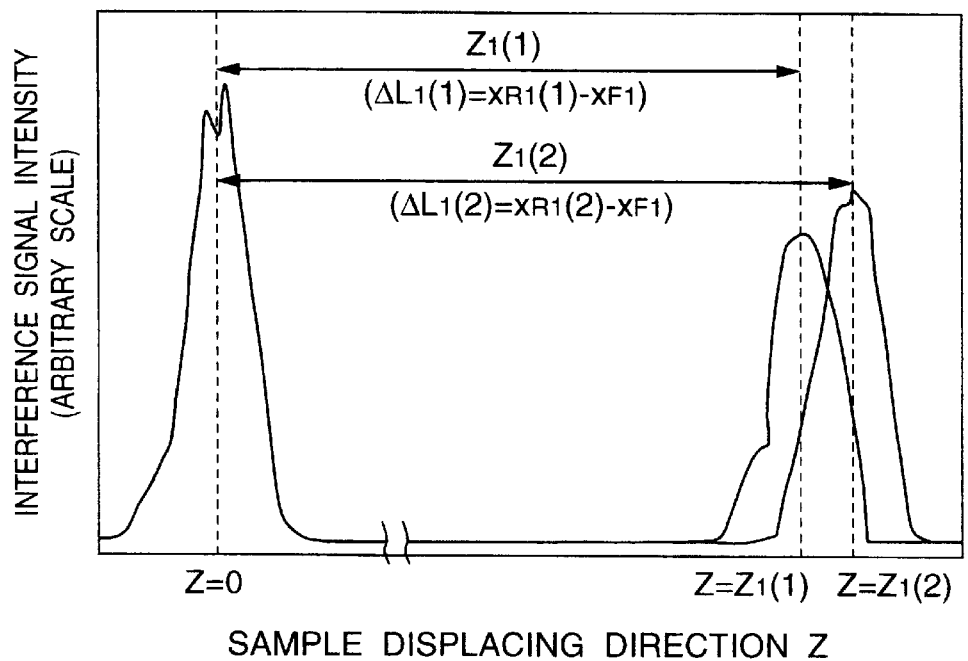
FIG. 10 is a graph showing examples of interference signals measured by the sample displacing process in a birefringence measuring method in an embodiment of the present invention.

Further, the birefringence n and the thickness t can be simultaneously measured. If nonpolarized light or random-polarized light is projected onto the object 4 to be measured having a birefringency (such as X-cut lithium niobate (LN) having the X-axis of crystal which perpendicular to the surface), as shown in FIG. 10, the light is splited into two liner polarized optical waves corresponding to a ordinary rays and an extraordinary rays which are polarized in the direction of the principal axis of the object 4 to be measured, and accordingly, the in-plane birefringence ($n_e$, $n_o$ or a difference therebetween) and the thickness t can be simultaneously measured without the necessity of porlarization control of a polarizer/analyzer, a polarizing rotator and the like.

That is, in the case of the object 4 to be measured having a birefringency, as shown in FIG. 4, the light is focused at the front surface of the object 4 to be measured (position z=0 of the drive means 5: focus point F'), and in this condition, the position of the reference light mirror 6 (the position $x = x_{F1}$ of the drive means 7) where a maximum interference signal intensity can be obtained is detected and digitalized by the detection circuit 11 and is then delivered to the PC 13, and further, the drive means 5 is moved so as to obtain data around $x_{F1}$ in order to specify $x_{F1}$ which exhibits a maximum optical interference intensity. Next, using the drive means 5, the object 4 to be measured is displaced toward the converging lens 3 so as to specify two points (z=$z_1$(1), $z_1$(2); focus point F) corresponding respectively to a ordinary rays and an extraordinary rays which are produced due to the characteristics of the object 4 to be measured having a birefringence and which are focused to the rear surface of the object 4 to be measured (refer to FIG. 10). As to these conditions z=$z_1$(1), $z_1$(2), the drive means 7 is adjusted so as to cause the interference signal intensity to be again maximum, and the positions x=$x_{R1}$(1), $x_{R2}$(2) corresponding respectively to them are specified, similar to $x_{F1}$. The optical path difference between two conditions in which the focusing is made to both front and rear surfaces) is given by $\Delta L_1(1) = x_{R1}(1) - x_{F1}$, $\Delta L_1(2) = x_{R1}(2) - x_{F1}$, and from two independent measured values corresponding to $\Delta L_1(1)$, $\Delta L_1(2)$ and $z_1(1)$, $z_1(2)$, a birefringence ($n_e$, $n_o$ or a difference therebetween) in the surfaces of the object 4 to be measured, and a thickness t thereof can be obtained.

From the above-mentioned measurements, a desired value $\Delta L_1$ (=$x_{R1} - x_{F1}$) can be obtained, and the refractive index (birefringence) n and the thickness t of the object 4 to be measured can be calculated from EQ4 and EQ5.

However, since low coherent light having oscillating wavelength diversion has to be considered as a wave packet, the thus obtained refractive index n is a refractive index (=group index ng) including wavelength dispersion of the refractive index of the object to be measured. Since the Snell's law is dependent upon the phase index np while this optical path length of the interferometer is dependent upon the group index np, from EQ2, $$z_1 = t \times \sqrt{\frac{1 - \zeta^2}{n_p^2 - \zeta^2}} \quad \text{EQ6}$$

$$\zeta = \sin\theta$$

-continued $$\Delta L_1 + z_1 = n_g \times t \quad \text{EQ7}$$

where $$n_g = n_p + \lambda_c \cdot \left|\left(\frac{dn}{d\lambda}\right)_{\lambda_c}\right| \equiv n_p + \Delta n_1 \quad \text{EQ8}$$

where $\lambda c$ is the center oscillating wavelength of the light source. From EQ6 to EQ8, t is eliminated, and as a linear expression of $\delta$ $$n_p^2 = \frac{1}{2}\left\{\zeta^2 + \sqrt{\zeta^4 + 4(1-\zeta^2)\left(1 + \frac{\Delta L_1}{z_1}\right)^2 (1 - 2\delta n_1)}\right\} \quad \text{EQ9}$$

$$\delta n_1 = \frac{\Delta n_1}{n_p} = \frac{\lambda_c \cdot \left|\left(\frac{dn}{d\lambda}\right)_{\lambda_c}\right|}{n_p} \quad \text{EQ10}$$

cab be obtained.

A correction term $2\delta n_1$ included in EQ9, is inherently unknown, and accordingly, np cannot be calculated. Accordingly, it is required to examine a relationship between the wavelength dispersion and the phase index (refer to FIG. 7) through experiments. An object to be measured, which is to be examined, has a measured wavelength range which is far away from the absorption end, and according exhibits a normal dispersion (dispersion given by a Sellmeier's equation) From FIG. 7, it is understood that np and np/d$\lambda$ have an exponential relationship therebetween. Accoring, in view of such a fact that the dispersion is zero in the atmospheric pressure (np=1), $\delta n_1$ can be exhibited as follows with respect to np.

$$\delta n_1 = a \cdot (n_p - 1)^b \quad \text{EQ11}$$

where a, b can be determined through experiments. Approximation is made such as $\zeta^2 \ll 1$ and $n_1 \ll 1$, an first order approximation of np is given by:

$$n_p^2 \approx 1 + \frac{\Delta L_1}{z_1} \quad \text{EQ12}$$

From EQ11 and EQ12, $\delta n_1$ can be exhibited only by experimental values $\Delta L_1$ and $z_1$ as follows:

$$\delta n_1 = a \cdot \left(\sqrt{1 + \frac{\Delta L_1}{z_1}} - 1\right)^b \quad \text{EQ13}$$

and np and t can be calculated from the two values $\Delta L_1$ and $z_1$ with the use of EQ9, EQ13 and EQ6. However, NA ($\zeta$) of the converging lens can be obtained by measuring a sample having a thickness t and a phase index np which are known and by using the following equation:

$$\zeta = \sqrt{\frac{t^2 - n_p^2 \cdot z_1^2}{t^2 - z_1^2}} \quad \text{EQ14}$$

In order to determine the constants a, b, np, ng and a difference $\delta n_1$ therebetween are obtained through experiments of an object to be measured having a known t, and thus measured values ($\delta n_1$, np−1) are ploted on a logarithmic graph. That is, both sides of EQ1 is logarithmically expressed as follows:

$$\log(\delta n_1) = \log(a) + b \cdot \log(n_p - 1) \qquad \text{EQ15}$$

and accordingly, b can be determined from a gradient and a can be determined from an intercept. However, $\zeta$ and t are known in this measurement, from EQ6 and EQ7 the following equations can be obtained:

$$n_p = \sqrt{\zeta^2 + (1-\zeta^2)\left(\frac{t}{z_1}\right)^2} \qquad \text{EQ16}$$

$$n_g = \frac{\Delta L_1 + z_1}{t} \qquad \text{EQ17}$$

$$\delta n_1 = \frac{\Delta n_1}{n_p} = \frac{1}{n_p}(n_g - g_p) \qquad \text{EQ18}$$

In the method as mentioned above, when a, b are determined, NA($\zeta$) of the converging lens exhibited by an arithmetic equation EQ9 including the correction term $\zeta n_1$ can be calibrate. EQ9 can rewritten into $$\zeta_i = \sqrt{\frac{n_p^4 - \left(1 + \frac{\Delta L_1}{z_1}\right)^2 \cdot (1 - 2\delta n_1)}{n_p^2 - \left(1 + \frac{\Delta L_1}{z_1}\right)^2 \cdot (1 - 2\delta n_1)}} \qquad \text{EQ19}$$

and in EQ19, $\delta n_1$ is given from EQ13 and the values a, b are given from EQ15.

If the calibration value of $\zeta_i$ is determined, from the actually measured values ($z_1$, $\Delta L_1$) by using the following equation $$n_p^2 = \frac{1}{2}\left\{\zeta_i^2 + \sqrt{\zeta_i^4 + 4(1-\zeta_i^2)\left(1 + \frac{\Delta L_1}{z_1}\right)^2 (1 - 2\delta n_1)}\right\} \qquad \text{EQ20}$$

the phase index np can be obtained, and t can be obtained from the following equation which is obtained by rewriting EQ6:

$$t = z_1 \cdot \sqrt{\frac{n_p^2 - \zeta_i^2}{1 - \zeta_i^2}} \qquad \text{EQ21}$$

Thus, in order to obtain the phase index np and the thickness t of the object 4 to be measured, and the birefringence (np or $\Delta$np) and the thickness thereof, several transparent materials having known thicknesses t and phase refractive indices np have been previously measured, and by determining a, b in EQ13, and by using EQ19 so as to calibrate NA($\zeta$) of the converging lens, the position of the reference light mirror 6 (position x=$x_{F1}$ of the drive means 7) where a maximum interference signal intensity can be obtained in a condition such that the focusing is made at the front surface of the object 4 to be measured (position z=0 of the drive means 5; focus point F'), is detected and digitalized by the detecting circuit 11, and is delivered to PC 13, and further, the drive means 5 is moved so as to obtain data around $x_{F1}$ in order to specify $x_{F1}$ where a maximum interference signal intensity is obtained. Next, the object 4 to be measured is moved toward the converging lens 3 by the distance $z_1$ with the use of the drive means 5 (focusing at the rear surface of the object 4 to be measured, z=$z_1$: focus point F), and in this condition, the position thereof x=$x_{R1}$ is specified similar to $x_{F1}$ by adjusting the drive means 7 so as to maximing the intensity of the interference signal. The optical path difference between two condition in which focusing is made at both front and rear surfaces is given by $\Delta L_1 = x_{R1} - x_{F1}$, and from these two independent values $\Delta L_1$, $z_1$, using EQ20, EQ13 and EQ21, the phase index np and the thickness t of the object 4 to be measured can be calculate.

Similarly, in the case of the object 4 to be measured having a birefringency referring to FIG. 4, the position of the reference mirror (position x=$x_{F1}$ of the drive means 7) where a maximum interference signal intensity can be obtained in a condition in which focusing is made at the front surface of the object 4 to be measured (position z=0; focus point F') is detected and digitalized by the detecting circuit 11 and is delivered to PC 13, and further, the drive means 5 is moved so as to obtain data around $x_{F1}$ in order to specify $x_{F1}$ where a maximum interference signal intensity is obtained. Next, the object 4 to be measured is moved toward the converging lens 3 by the distance $z_1$ with the use of the drive means 5 (focusing at the rear surface of the object 4 to be measured, z=$z_1$: focus point F), and in this condition, the position thereof x=$x_{R1}$ is specified similar to $x_{F1}$. Next, using the drive means 5, the object 4 to be measured is displaced toward the converging lens 3 so as to specify two points (z=$z_1$(1), $z_1$(2); focus point F) corresponding respectively to a ordinary rays and an extraordinary rays which are focused at the rear surface of the object 4 to be measured due to the characteristics of the object 4 to be measured having a birefringence (refer to FIG. 10). As to these conditions z=$z_1$(1), $z_1$(2), the drive means 7 (reference light mirror 6) is adjusted so as to cause the interference signal intensity to be again maximum, and the positions x=$x_{R1}$(1), $x_{R2}$(2) corresponding respectively to them are specified, similar to $x_{F1}$. The optical path difference between two conditions in which the focusing is made to both front and rear surfaces is given by $\Delta L_1(1) = x_{R1}(1) - x_{F1}$, $\Delta L_1(2) = x_{R1}(2) - x_{F1}$, and from two independent measured values corresponding to $\Delta L_1(1)$, $\Delta L_1(2)$ and $z_1(1)$, $z_1(2)$, a birefringence ($n_e$, $n_o$ or a difference therebetween) in the surfaces of the object 4 to be measured, and a thickness t thereof can be obtained by using EQ20, EQ13 and EQ21.

Further, as to an object to be measured having a known thickness, two independent measured values $\Delta L_1$, $z_1$ obtained similarly as mentioned above are substituted together with $\zeta$ obtained by EQ14, into EQ16 and EQ17. The phase index np and the group index ng of the object 4 to be measured can be calculated.

It is noted if a light source 1 and a converging lens 3 which are similar to those mentioned above, are used, $\zeta$, the constants a, b and $\zeta i$ can be used as values obtained in a lens displacing process which will be hereinbelow detailed.

1)-2 Lens Displacing Process

Explanation will be made of a lens displacing process with reference to FIGS. 2, 3, 5, 8 and 11.

Figure 2C:
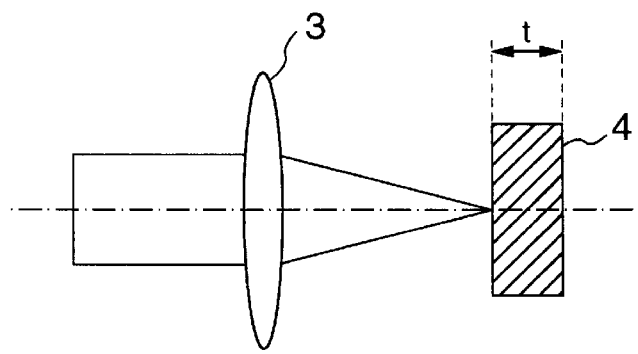
Figure 2D:
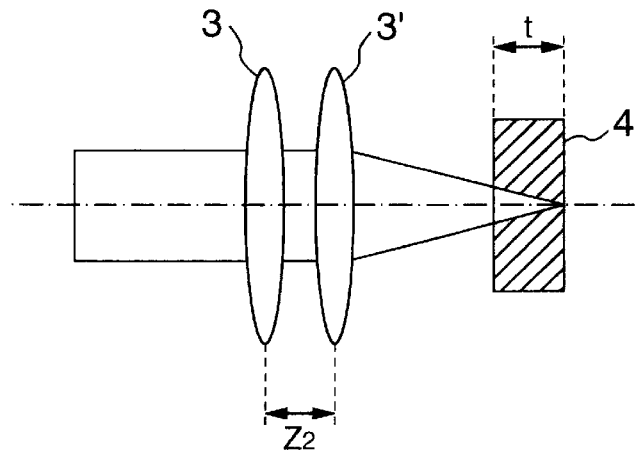
Figure 3C:
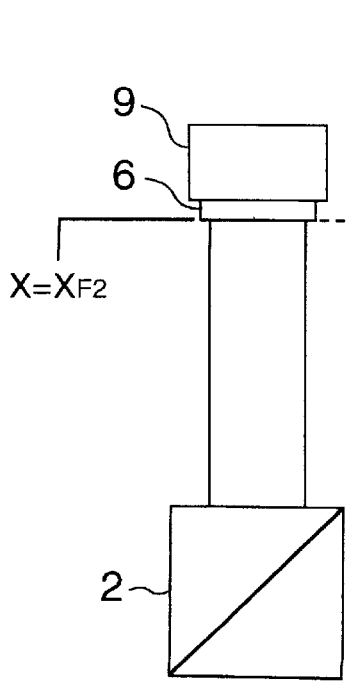
Figure 3D:
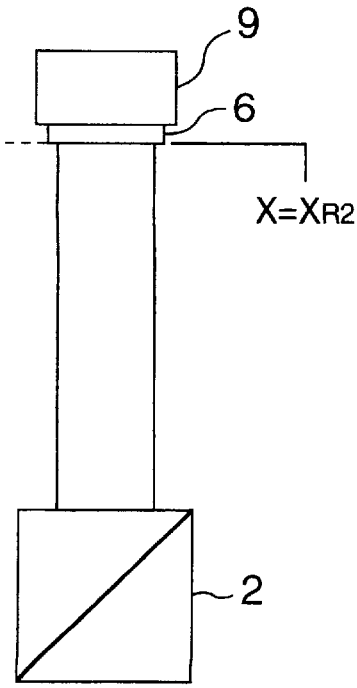
Figure 8A:
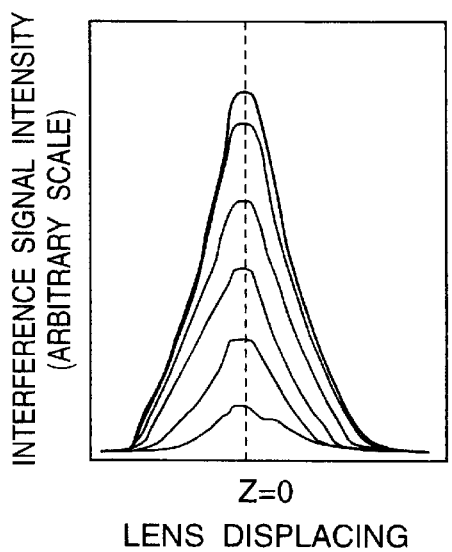
FIGS. 8a and 8b are views showing interference intensities at front and rear surfaces, which are measured by the lens displacing process in an embodiment of the present invention.
Figure 8B:
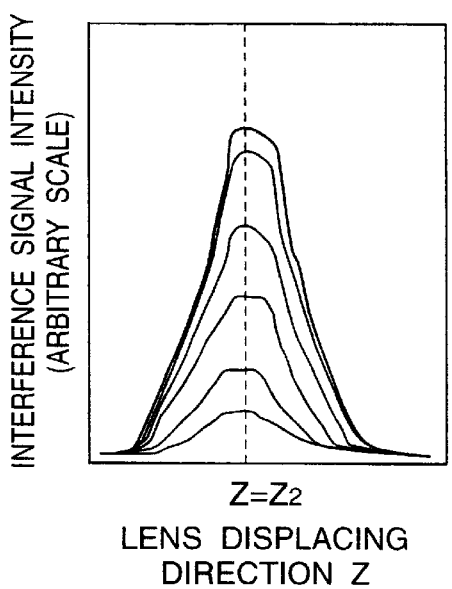

In the lens displacing process, as shown in FIG. 2c, light from the light source 1 is converged onto the front surface of the object 4 to be measured, and then, as shown in FIG. 3c, the position of the reference light mirror 6 is adjusted by the drive means 7 so as to set the difference between the optical path lengths of the reference light beam and the signal light arm to zero. As shown in FIG. 3c, the position of the reference light mirror 6 is adjusted by the drive means 7. FIG. 8a shows intensity patterns of interference signals which are obtained when the position of the reference light mirror 6 is displaced at predetermined intervals while the converging lens 3 is displaced by means of a drive means 8 after the light beam from the converging lens 3 is focused at a position in the vicinity of the object 4 to be measured. From the position where the intensity of the interference signal becomes maximum, z=0 is determined, and the position of the reference light mirror 6 (drive means 7) corresponding thereto is x=$x_{F2}$. Next, as shown in FIG. 2d, the drive means 8 is moved so as to cause the converging lens 3 to approach the object 4 to be measured so that the light beam is focused onto the rear surface of the object to be measured. Then, as shown in FIG. 3d, the reference mirror 6 is moved by $\Delta L_2$ by the drive means 7 so as to the optical path difference between two arms of the interferometer becomes again zero in this condition. FIG. 8b shows intensity patterns of interference signals which are obtained when the position of the reference light mirror 6 is displaced at predetermined intervals while the converging lens 3 is displaced by the drive means 8 after the light beam from the converging lens 3 is focused in the vicinity of the rear surface of the object 4 to be measured, From a position where the intensity of the interference signal becomes maximum, z=$z_2$ is determined, and the position of the reference light mirror 6 (drive means 7) corresponding thereto is x=$x_{R2}$.

Figure 5:
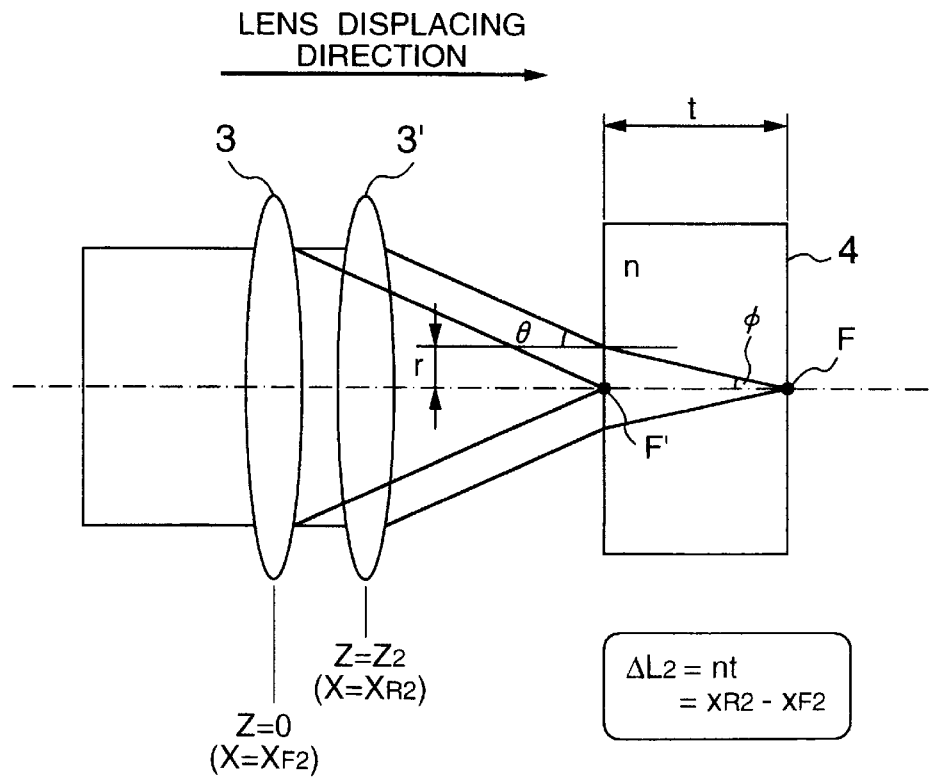
FIG. 5 is a view for explaining a principle of the lens displacing process in an embodiment of the present invention.

FIG. 5 shows a principle view for explaining the lens displacing process. Accordingly, it is found that $$z_2 = t\sqrt{\frac{1-\zeta^2}{n^2-\zeta^2}} \quad \text{EQ22}$$

can be obtained. Further, $\Delta L_2$ exhibits an optical path length between the focus points F, F' at the front and rear surfaces of the object 4 to be measured, and accordingly, becomes constant, regardless of $z_2$, that is:

$$\Delta L_2 = n \times t \quad \text{EQ23}$$

Thus, in such a case that the object 4 to be measured stationary with respect to the branching and synthesizing means 2 for receiving light from the light source, it should be noted that the optical path difference $\Delta L_2$ is not changed even though the converging lens 3 therebetween is displaced. From EQ22 and EQ23, the refractive index n can be given by:

$$n^2 = \frac{1}{2}\left\{\zeta^2 + \sqrt{\zeta^4 + 4(1-\zeta^2)\left(\frac{\Delta L_2}{z_2}\right)^2}\right\} \quad \text{EQ24}$$

and the thickness t can be give by:

$$t = \frac{\Delta L_2}{n} \quad \text{EQ25}$$

That is, referring to FIG. 5, the light beam is converged to the front surface of the object 4 to be measured (the position z=0 of the drive means 8, focus point F'), and then the position (the position x=$x_{F2}$ of the drive mean 7) of the reference light mirror 6 is specified as in the sample displacing process. Then the object 4 to be measured is moved toward the converging lens 3 by the distance $z_2$ for focusing at the rear surface of the object 4 to be measured (z=$z_2$: focus point F). In this condition, the drive means 7 is adjusted so as to cause the interference signal intensity to be again maximum in order to specify the position thereof x=$x_{R2}$, similar to the above-mentioned sample displacing process. The optical path difference between two conditions in which focusing is made at the front and rear surfaces is given by $\Delta L_2 = x_{R2} - x_{F2}$, and accordingly, from these two independent values $\Delta L_2$, $z_2$, the refractive index n and the thickness t of the object 4 to be measured can be obtained.

Figure 11:
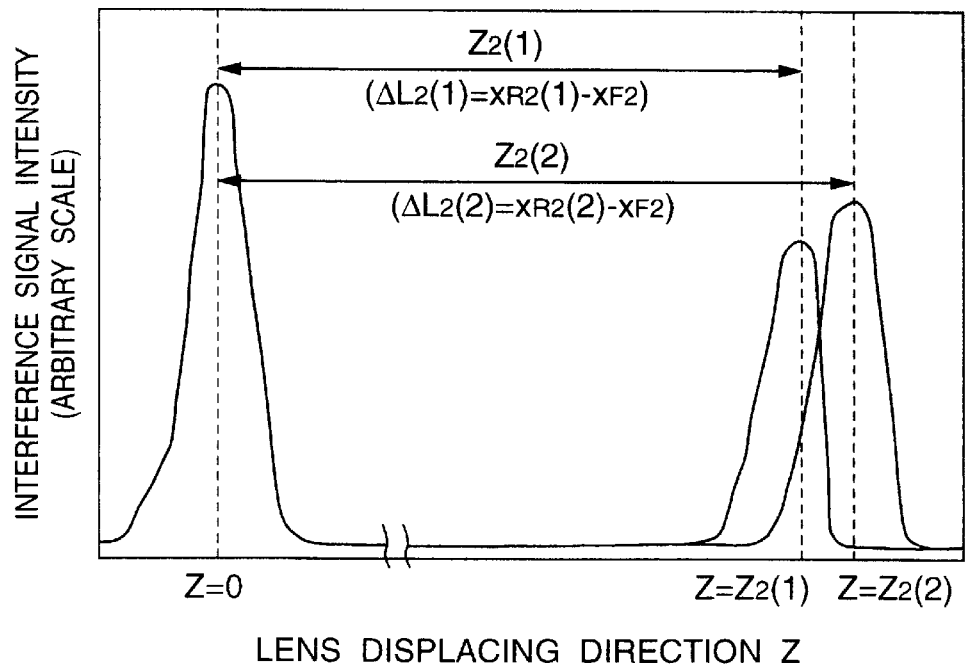
FIG. 11 is a graph showing examples of interference signals measured by the lens displacing process in a birefringence measuring method in an embodiment of the present invention.

Further, the birefringence n and the thickness t can be simultaneously measured. If unpolarized light or random-polarized light is projected into the object 4 to be measured having a birefringency (such as X-cut lithium niobate (LN) having the X-axis of crystal which perpendicular to the surface), as shown in FIG. 11, the light is split into two linearly polarized optical waves corresponding to an ordinary rays and an extraordinary rays which are polarized in the direction of the principal axis of the object 4 to be measured, and accordingly, the in-plane birefringence ($n_e$, $n_o$ or a difference therebetween) and the thickness t can be simultaneously measured without the necessity of polarization control of a polarizer/analyzer, a polarizing rotator and the like.

That is, in the case of the object 4 to be measured having a birefringency, as shown in FIG. 5, the light is focused at the front surface of the object 4 to be measured (position z=0 of the drive means 8: focus point F), and in this condition, data around the x=$x_{F2}$ are obtained so as to specify the position of the reference light mirror 6 where a maximum interference signal intensity can be obtained (position x=$x_{F2}$ of the drive means 7), similarly as mentioned above. Next, using the drive means 8, the converting lens 3 is moved toward the object 4 to be measured so as to specify two points (z=$z_2$(1), $z_2$(2); focus point F) corresponding respectively to ordinary rays and an extraordinary rays which are produced due to the characteristics of the object 4 to be measured having a birefringence and which are focused to the rear surface of the object 4 to be measured (refer to FIG. 11). As to these conditions z=$z_2$(1), $z_2$(2), the drive means 7 (reference light mirror 6) is adjusted so as to cause the interference signal intensity to be again maximum, and the positions x=$x_{R2}$(1), $x_{R2}$(2) corresponding respectively to them are specified. The optical path difference between two conditions in which the focusing is made to both front and rear surfaces) is given by $\Delta L_2(1) = x_{R2}(1) - x_{F2}$, $\Delta L_2(2) = x_{R2}(2) - x_{F2}$, and from two independent measured values corresponding to $\Delta L_2(1)$, $\Delta L_2(2)$ and $z_2(1)$, $z_2(2)$, a birefringence ($n_e$, $n_o$ or a difference therebetween) in the surfaces of the object 4 to be measured, and a thickness t thereof can be obtained.

From the above-mentioned measurements, a desired value $\Delta L_2$ (=$x_{R2} - x_{F2}$) and $z_2$ can be obtained, and the refractive index (birefringence) n and the thickness t of the object 4 to be measured can be calculated from EQ24 and EQ25.

However, it should be noted that the refractive index n thus obtained is a group index as is similar to the sample displacing process. Low coherent light having a wide oscillating wavelength range, as a light source, should be considered as a wave packet, and accordingly, the refractive index n which can be obtained in the above-mentioned measurement is a refractive index (group index ng) including wavelength dispersion of the refractive index of the object to be measured. Accordingly, in consideration with the wavelength dispersion of the refractive index of the object to be measured:

$$z_2 = t\sqrt{\frac{1-\zeta^2}{n_p^2-\zeta^2}} \quad \text{EQ26}$$

can be obtained.

Further, since $\Delta L_2$ is a optical path difference between the focus points F, F' at the front and rear surfaces of the object to be measured, and is constant regardless of $z_2$, that is, it is given by:

$$\Delta L_2 = n_g \times t \quad \text{EQ27}$$

Further, $$n_g = n_p + \lambda_c \cdot \left|\left(\frac{dn}{d\lambda}\right)_{\lambda_c}\right| \equiv n_p + \Delta n_2 \quad \text{EQ28}$$

where $\lambda c$ is the oscillating center wavelength of the light source. It is eliminated from EQ26, EQ27 and EQ28, and the following first-order approximation formulae:

$$n_p^2 = \frac{1}{2}\left\{\zeta^2 + \sqrt{\zeta^4 + 4(1-\zeta^2)\left(\frac{\Delta L_2}{z_2}\right)^2(1-2\delta n_2)}\right\} \quad \text{EQ29}$$

$$\delta n_2 = \frac{\Delta n_2}{n_p} = \frac{\lambda_c \cdot \left|\left(\frac{dn}{d\lambda}\right)_{\lambda_c}\right|}{n_p} \quad \text{EQ30}$$

can be obtained.

A correction term $2\delta n_1$ included in EQ29, is inherently unknown since the wavelength dispersion is unknown, and accordingly, np cannot be calculated. Accordingly, it is required to examine a relationship between the wavelength dispersion and the phase index through experiments as similar to the sample displacing process. Accordingly, in view of such a fact that the dispersion is zero in the atmospheric pressure (np=1), $\delta n_2$ can be exhibited as follows with respect to np.

$$\delta n_2 = a \cdot (n_p - 1)^b \quad \text{EQ31}$$

where a, b can be determined through experiments. Approximation is made such as $\zeta^2 \ll 1$ and $n_2 \ll 1$, an first approximation of np is given by:

$$n_p^2 \approx \frac{\Delta L_2}{z_2} \quad \text{EQ32}$$

From EQ31 and EQ32, $\delta n_2$ can be exhibited only by experimental values $\Delta L_2$ and $z_2$ as follows:

$$\delta n_2 = a \cdot \left(\sqrt{\frac{\Delta L_2}{z_2}} - 1\right)^b \quad \text{EQ33}$$

and np and t can be calculated from the two values $\Delta L_2$ and $z_2$ with the use of EQ29, EQ33 and EQ26. However, NA($\zeta$) of the converging lens can be obtained by measuring a sample having a thickness t and a phase index np which are known and by using the following equation:

$$\zeta = \sqrt{\frac{t^2 - n_p^2 \cdot z_2^2}{t^2 - z_2^2}} \quad \text{EQ34}$$

In order to determine the constants a, b, np, ng and a difference $\delta n_2$ therebetween are obtained through experiments of an object to be measured having a known t, and thus measured values ($\delta n_2$, np–1) are ploted on a logarithmic graph. That is, both sides of EQ31 is logarithmically expressed as follows:

$$\log(\delta n_2) = \log(a) + b \cdot \log(n_p - 1) \quad \text{EQ35}$$

and accordingly, b can be determined from a gradient and a be determined from an intercept. However, $\zeta$ and t are known in this measurement, from EQ26 and EQ27 the following equations can be obtained:

$$n_p = \sqrt{\zeta^2 + (1-\zeta^2)\left(\frac{t}{z_2}\right)^2} \quad \text{EQ36}$$

$$n_g = \frac{\Delta L_2}{t} \quad \text{EQ37}$$

$$\delta n_2 = \frac{\Delta n_2}{n_p} = \frac{1}{n_p}(n_g - n_p) \quad \text{EQ38}$$

In the method as mentioned above, when a, b are determined, NA($\zeta$) of the converging lens exhibited by an arithmetic equation EQ29 including the correction term $\zeta n_2$ can be calibrated. EQ29 can rewritten into $$\zeta_i = \sqrt{\frac{n_p^4 - \left(\frac{\Delta L_2}{z_2}\right)^2 \cdot (1 - 2\delta n_2)}{n_p^2 - \left(\frac{\Delta L_2}{z_2}\right)^2 \cdot (1 - 2\delta n_2)}} \quad \text{EQ39}$$

and in EQ39, $\delta n_2$ is given from EQ33 and the values a, b are given from EQ35.

If the calibration value of $\zeta_i$ is determined, from the actually measured values ($z_2$, $\Delta L_2$) by using the following equation $$n_p^2 = \frac{1}{2}\left\{\zeta_i^2 + \sqrt{\zeta_i^4 + 4(1-\zeta_i^2)\left(\frac{\Delta L_2}{z_2}\right)^2(1-2\delta n_2)}\right\} \quad \text{EQ40}$$

the phase index np can be obtained, and t can be obtained from the following equation which is obtained by rewriting EQ26:

$$t = z_2 \sqrt{\frac{n_p^2 - \zeta_i^2}{1 - \zeta_i^2}} \quad \text{EQ41}$$

Accordingly, in order to obtain the phase index np and the thickness of the object 4 to be measured, and the birefringence (np or $\Delta$np) and the thickness thereof, several kinds of transparent materials having thicknesses t and phase refractive indices which are well-known, have been previously measured so as to determine the constants a, b in EQ33, and then NA ($\zeta$) of the converging lens is calibrated with the use of EQ39. Thus, referring to FIG. 5, the light beam is converged to the front surface of the object 4 to be measured (the position z=0 of the drive means 8, focus point F'), and then the position (the position x=$x_{F2}$ of the drive mean 7) of the reference light mirror 6, where a maximum intensity of an interference signal can be obtained is specified as in the sample displacing process. Then the converging lens 3 is moved to the object 4 to be measured by the distance $z_2$ with the use of the drive means 8 for focusing at the rear surface of the object 4 to be measured (z=$z_2$: focus point F). In this condition, the drive means 7 (reference mirror 6) is adjusted so as to cause the interference signal intensity to be again maximum in order to specify the position thereof x=$x_{R2}$, similar to the above-mentioned sample displacing process. The optical path difference between two conditions in which focusing is made at the front and rear surfaces is given by $\Delta L_2 = x_{R2} - x_{F2}$, and accordingly, from these two independent values $\Delta L_2$, $z_2$, the phase index np and the thickness t of the object 4 to be measured can be obtained with the use of EQ40, EQ33 and EQ41.

Similarly, in the case of the object 4 to be measured having a birefringency, as shown in FIG. 5, the light is focused at the front surface of the object 4 to be measured (position z=0 of the drive means 8: focus points F'), and in this condition, data around the $x=x_{F2}$ are obtained so as to specify the position of the reference light mirror 6 where a maximum interference signal intensity can be obtained (position $x=x_{F2}$ of the drive means 7), similarly as mentioned above. Next, using the drive means 8, the converting lens 3 is moved toward the object 4 to be measured so as to specify two points ($z=z_2(1)$, $z_2(2)$; focus point F) corresponding respectively to an ordinary rays and an extraordinary rays which are produced due to the characteristics of the object 4 to be measured having a birefringence and which are focused to the rear surface of the object 4 to be measured (refer to FIG. 11). As to these conditions $z=z_2(1)$, $z_2(2)$, the drive means 7 (reference light mirror 6) is adjusted so as to cause the interference signal intensity to be again maximum, and the positions $x=x_{R2}(1)$, $x_{R2}(2)$ corresponding respectively to them are specified. The optical path difference between two conditions in which the focusing is made to both front and rear surfaces is given by $\Delta L_2(1)=x_{R2}(1)-x_{F2}$, $\Delta L_2(2)=x_{R2}(2)-x_{F2}$, and from two independent measured values corresponding to $\Delta L_2(1)$, $\Delta L_2(2)$ and $z_2(1)$, $z_2(2)$, a birefringence ($n_e$, $n_o$ or a difference therebetween) in the surfaces of the object 4 to be measured, and a thickness t thereof can be obtained with the use of EQ40, EQ33 and EQ41.

Further, as to an object to be measured having a known thickness, the two independent measured values $\Delta L_2$, $z_2$ which are measured as mentioned above are substituted in EQ36 and EQ37 together with $\zeta$ obtained by EQ34, the phase index $n_p$ and the group phase index ng of the object 4 to be measured can be calculated.

It is noted that $\zeta$, the constants a, b and $\zeta i$ can be obtained by using values obtained in the sample displacing process if a light source and a converging lens which are similar to the light source 1 and the converting lens 3, respectively.

2) As to a method of measuring a birefringence of an object to be measured, the following two methods can be used.

Sample Displacing Process:

The reference light mirror is made to be stationary, and the object to be measured is displaced in the direction of the optical axis.

Reference Mirror Displacing Process:

The object to be measured is made to be stationary, and the reference light mirror is displaced in the direction of the optical axis.

Figure 12:
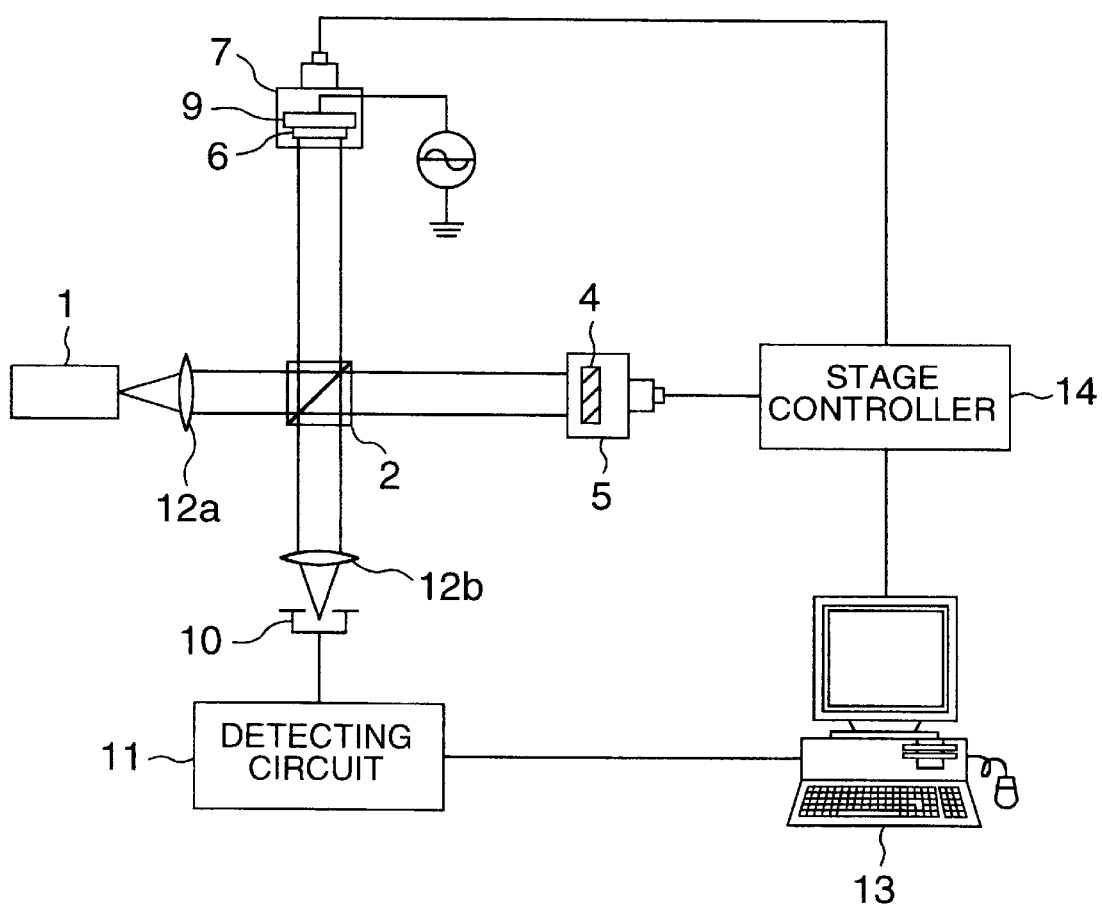
FIG. 12 is a block diagram illustrating a basic system for measuring a birefringence in an embodiment of the present invention.
Figure 14:
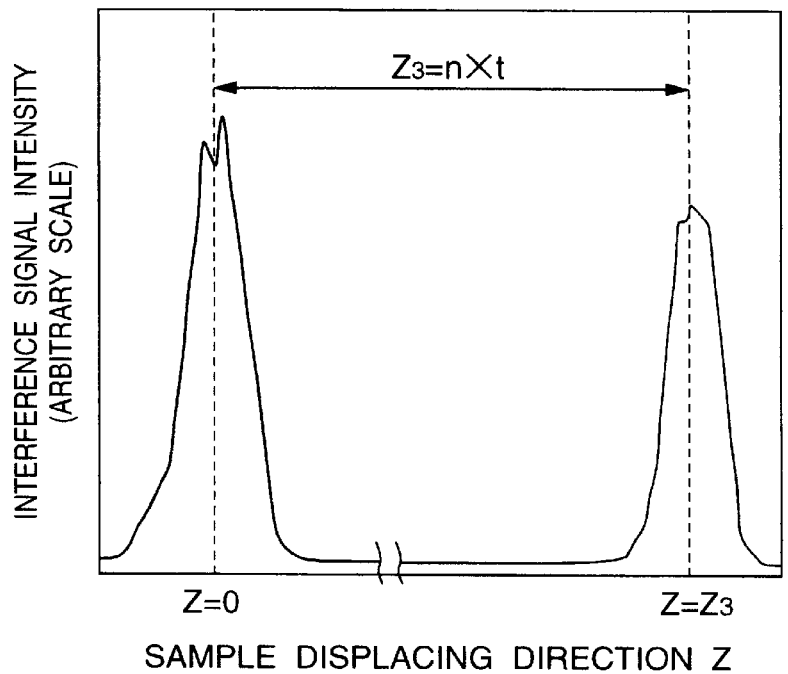
FIG. 14 is a graph for explaining the sample displacing process in the birefringence measuring method in an embodiment of the present invention.

FIG. 12 is a block diagram illustrating basic system for measuring a birefringence in an embodiment of the present invention. In FIG. 12, like reference numerals are used to denote like components shown in FIG. 1. Referring to FIG. 12 in which only difference from FIG. 1 is such that the converging lens 3 and the drive means 8 for holding and mounting the converging lens 3 are eliminated, light emitted from a light source 1 is led into a light branching and synthesizing means 2 for branching and synthesizing the light from the light source 1 through a lens 12a, the light is therefore equally divided into two branch beams one of which advances straightforward and is irradiated onto an object 4 to be measured which is held and mounted on a drive means 5. On the contrary, the other one of the branching beams advances at a right angle from the branching and synthesizing means 2 and is irradiated onto a reference light mirror 6 which is held and mounted to a drive means 7 and is fixed to a vibrator 9 which is applied thereto with vibration having a frequency f and a predetermined amplitude so as to phase-modulate a reflected beam (reference beam) from the reference light mirror 6. A reflected beam (signal beam) from the object 4 to be measured, and the reflected beam (reference beam) from the reference light mirror 6 are synthesized by the branching and synthesizing means 2, then is led through the lens 12b and detected by the light receiving element 10. A detection signal from the light receiving element 10 is converted into a digital signal by a detecting circuit 11, and data from the detecting circuit 11 are delivered to and processed by a PC 13.

2)-1 Sample Displacing Process

A sample displacing process will be explained with reference to FIGS. 13a to 13c, 14 and 15.

In this sample displacing process, as shown in FIG. 13a, unpolarized light or random polarized light are irradiated onto the object 4 to be measured, and the object 4 to be measured is displaced by the drive means 5 so as to set the optical path difference between the arms of the light (signal light) reflected at the front surface of the object 4 to be measured and the reference light to zero. Then, data around x=0 are obtained so as to specify a position where a maximum interference signal intensity can be obtained (z=0) as mentioned above. Next, as shown in FIG. 13b, the drive means is moved so as to cause the object 4 to be measured to approach the branching and synthesizing means 2, and then the object 4 is moved by the drive mans 5 so that the optical path length of the arms of the reflected light (signal light) from the rear surface of the object 4 to be measured and the reference light becomes again zero. Accordingly, as mentioned above, data around $z=z_3$ are obtained so as to specify a position where a maximum interference signal intensity can be obtained. The displaced distance of the object 4 to be measured (drive means 5) at this time is set to $z_3$ which gives the optical path difference (refractive index n×thickness t) (refer to FIG. 14).

Figure 15:
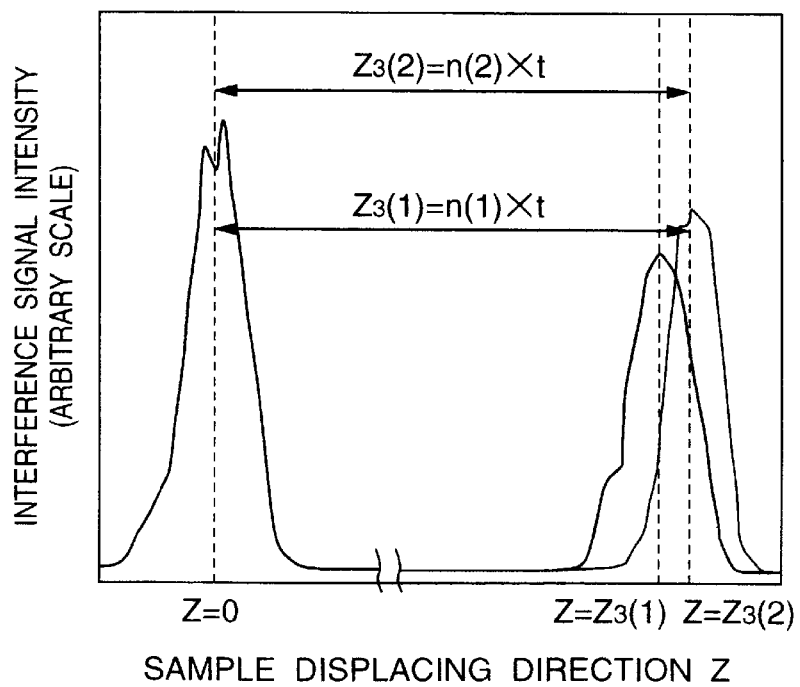
FIG. 15 is a graph illustrating examples of interference signals detected by the sample displacing process in the birefringence measuring method in an embodiment of the present invention.

In such a case that the object 4 to be measured is a medium having a birefringency, the drive means 5 is moved so as to cause the object 4 to be measured to approach the branching and synthesizing means 2, as shown in FIG. 15 (for example, X-cut lithium niobate (LN) having a crystal X-axis which is perpendicular to the surface), reflected light (signal light) which is split into two linear polarized light waves corresponding to the normal and extraordinary rays which are polarized in the direction of the principal axis due to the birefringency can be obtained from the rear surface of the object 4 to be measured.

That is, after the adjustment is made so that the optical path difference between the arms of the reference light and the signal light at the front surface of the object 4 to be measured becomes zero, as the object 4 to be measured is displaced toward the branching and synthesizing means 2, as shown in FIG. 15, the interference light intensity becomes a maximum at positions ($z_3(1)$, $z_3(2)$) of the object 4 to be measured, corresponding to the two linear polarized waves. Thus, data concerning the optical path lengths (refractive index n×thickness t) can be obtained. Thus, if the thickness t is known, the in-surface birefringence (one, no and a difference therebetween) of the object 4 to be measured can be evaluated.

It is noted that the thus obtained refractive index (birefringence) is a group index ng.

2)-2 Reference Mirror Displacing Process

Figure 16:
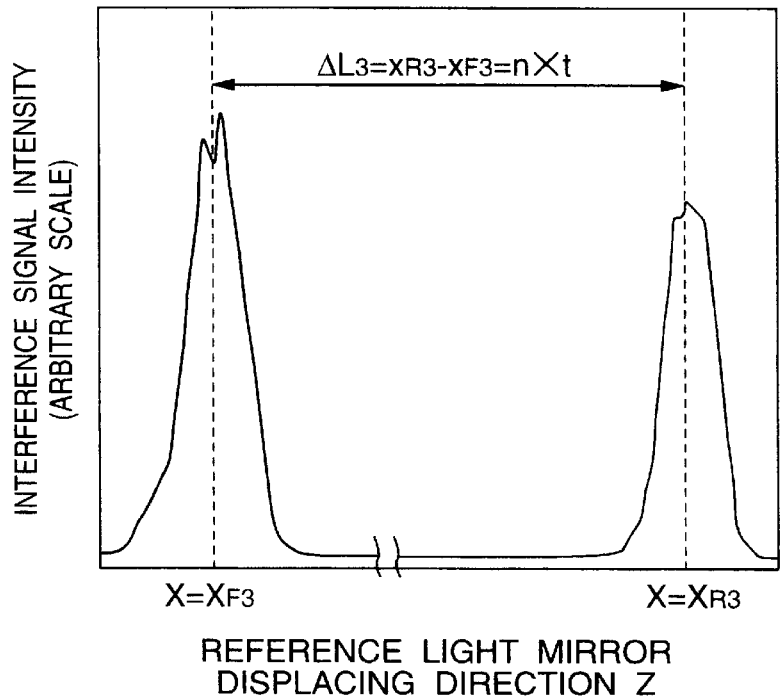
FIG. 16 is a graph for explaining a reference light mirror displacing process in the birefringence measuring method in an embodiment of the present invention.

A reference mirror displacing process will be hereinbelow explained with reference to FIGS. 13, 16 and 17.

In this reference mirror displacing process, as shown in FIG. 13c, unpolarized light or random polarized light are irradiated onto the object 4 to be measured, and the reference light mirror 6 is displaced by the drive means 7 so as to set the optical path difference between the arms of the light (signal light) reflected at the front surface of the object 4 to be measured and the reference light to zero. Then, data around $x=x_{F3}$ are obtained so as to specify a position where a maximum interference signal intensity can be obtained ($x=x_{F3}$) as mentioned above. Next, as shown in FIG. 13d, the drive means 7 is moved so as to cause the reference mirror 6 to go away from the branching and synthesizing means 2, and then the reference light mirror 6 is moved by the drive mans 7 so that the optical path length of the arms of the reflected light (signal light) from the rear surface of the object 4 to be measured and the reference light from the reference light mirror 6 becomes again zero. Accordingly, as mentioned above, data around $x=x_{R3}$ are obtained so as to specify a position where a maximum interference signal intensity can be obtained ($x=x_{R3}$). The displaced distance of the reference light mirror 6 (drive means 7) at this time is set to $\Delta L_3$ ($=x_{R3}-x_{F3}$) which gives the optical path difference (refractive index n×thickness t) (refer to FIG. 16).

Figure 17:
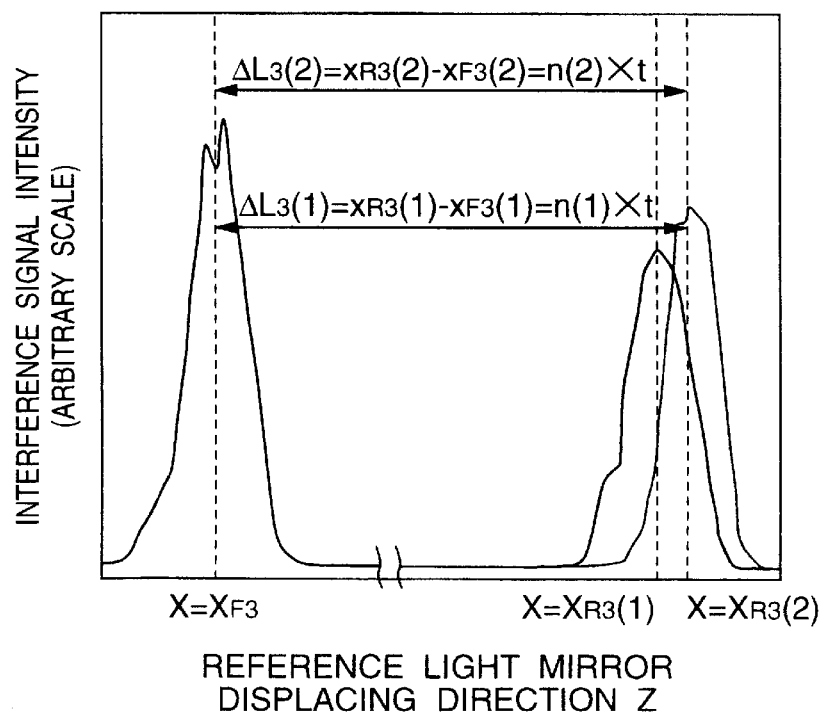
FIG. 17 is a graph showing examples of interference signal detected by the reference mirror displacing process in the birefringence measuring method in an embodiment of the present invention.

In such a case that the object 4 to be measured is a medium having a birefringency, the drive means 7 is moved so as to cause the reference light mirror 6 to go away from the branching and synthesizing means 2, as shown in FIG. 17 (for example, X-cut lithium niobate (LN) having a crystal X-axis which is perpendicular to the surface), reflected light (signal light) which is split into two linear polarized light waves corresponding to the normal and extraordinary rays which are polarized in the direction of the principal axis can be obtained from the rear surface of the object 4 to be measured.

That is, after the adjustment is made so that the optical path difference between the arms of the reference light and the signal light at the front surface of the object 4 to be measured becomes zero, as the object 4 to be measured is displaced toward the branching and synthesizing means 2, as shown in FIG. 17, the interference light intensity becomes a maximum at positions ($\Delta L_3(1)$, $\Delta L_3(2)$) of the object 4 to be measured, corresponding to the two linearly polarized waves. Thus, data concerning the optical path lengths (refractive index n×thickness t) can be obtained. Thus, if the thickness t is known, the in-surface birefringence ($n_e$, $n_o$ and a difference therebetween) of the object 4 to be measured can be evaluated.

It is noted that the thus obtained refractive index (birefringence) is a group index ng.

3) In order to evaluate a hardened condition or a hardness of hardenable resin, by using a refractive index which is averaged in the thicknesswise direction of the hardenable resin, as an evaluation index, at first, it is required to understand the characteristics of several kinds of hardenable resin. In general, the hardenable resin (ultraviolet ray-hardenable resin, thermohardenable resin, electron beam hardenable resin, catalyst hardenable resin, coating film and the like), changes (increases or decreases) its refractive index due to hardening and shrinkage or the like through a hardening progress from its liquid phase to a solid phase, and brings its to an equilibrium condition at a certain point. However, this change is up to about 0.02. Thus, in order to evaluate a hardened condition or a hardness of hardenable resin with the use of a refractive index, a high degree of resolution which is higher than the variation of the refractive index by one digit is required. Further, as to resin such as ultraviolet ray hardenable resin which undergoes its hardening from a surface where ultraviolet rays are irradiated, the hardening is greatly affected by a thickness of the resin,
various problems in the thicknesswise direction, such as nonuniform refractive index, intermingling of hardened parts and unhardened parts, and the like should be considered. In this case, it is required to use a refractive index which is averaged in the thicknesswise direction of the resin, as an evaluation index or it is required to precisely know a thickness of the resin. In consideration with these matters, in order to evaluate the hardening progress (hardened condition or a hardness) of resin from its liquid phase to its solid phase with a refractive index as an evaluation index, the simultaneous measurement of a refractive index and a thickness as stated in 1), that is, the sample displacing process or the lens displacing process, is used.

As to the light source 1, light having linear polarity, unlinear polarity or random polarity can be used for the simultaneous measurement of a refractive index and a thickness, and of a phase index and a group index. Further, unpolarized light and random polarized light can be used for measurement of a birefringence, and simultaneous measurement of a birefringence and a thickness. Specifically, those having a coherent length of less than 30 μm, including a superluminescent diode (SLD), the one which is obtained through spectroscopy of a white light source (halogen lamp or xenon lamp) by a nonchromator for a specific wavelength range, a laser diode (LD) excited by an inrush current lower than its threshold value, and a light emitting diode, can all be used. Further, the wavelength of the light source should not be limited, and accordingly, any light ranging from ultraviolet rays to infrared rays and having a coherent length of less than 30 μm can be used. Thus, with the use of the combination of a white light source and a monochromator, scanning can be carried out in a range from a short wavelength to a long wavelength so as to measure a wavelength characteristic (wavelength dispersion) of an object to be measured (medium), and further, with the use of a plurality of laser diodes having different oscillating center wavelengths can be used, similar to the light source in which light obtained by spectroscopy of white light by a monochromator, for measuring a wavelength characteristic (wavelength dispersion). It is preferable for measurement that the output of the light source is stable with no fluctuation, and can cope with a sensitivity of the light receiving element for synthesizing signal light from the object to be measured and reference light from the reference light mirror for interference therebetween, and detecting a detection signal.

The branching and synthesizing means 2 branches light from the light source 1 into two branch beams directed to the object 4 to be measured and the reference light mirror 6, and synthesizes reflected light (signal light) from the object 4 to be measured and reflected light (reference light) from the reference light mirror 6 so as to emit light to the light receiving element 10. Specifically, a beam splitter (BS), a chrome half-mirror, an aluminum half-mirror, a dielectric multilayer film half-mirror, a single mode fiber coupler, a light waveguide, a directive coupler or the like can be used. Inter alia, BS and the single mode fiber coupler are preferably used as the branching and synthesizing means in view of manipulatability for alignment of optical axes. However, the branching and synthesizing means 2 should not be limited to those as mentioned above, but any of those which can achieve the above-mentioned function can be used therefor. It goes without saying that the used wavelength of the branching and synthesizing means 2 must be optimized for a used wavelength of the light source 1 in order to minimize absorption and loss. Further, the branching and synthesizing means 2 is preferably coated with an antireflection (AR) coating in order to decrease the reflection of incident light as possible as it can so as to increase the volume of transmitted light. As to the AR coating, a multilayer coating is preferably used.

The converging lens 3 is the one which converges light from the branching and synthesizing means 3 onto the object 4 to be measured. A planoconvex lens, a biconvex lens, a cylindrical lens, a spherical lens or the like which is made of glass, inorganic materials such as optical crystal or polymer materials such as polymethyl-methaacrylate (PMMA) or polycarbonate (PC) can be used as the converging lens 3. Inter alia, a lens made of an inorganic material such as a lens made of BK7 having a high transmissivity for wavelength in an ultraviolet ray range and a near-infrared ray range, or a lens made of quartz having properties including g a high transmissivity for wavelengths in an ultraviolet ray range, a visual light range and a near-infrared ray range, a low thermal expansion coefficient and a thermal stability is preferably used as the converging lens 3. The converging lens 3 is preferably coated with an antireflection (AR) coating in order to decrease the reflection of incident light as possible as it can so as to increase the volume of transmitted light. As to the AR coating, a multilayer coating is preferably used. An objective lens used for a metal microscope may be used as the converging lens 3.

The object 4 to be measured, may includes glass (for example, quartz glass, soda-lime glass, borosilicated glass, lead glass or the like), polymer (for example, PMMA, PC, polyethylene terephatalate, polybutylene terephtahlate, methylmethaacrylate, epoxy resin, polyfluoroacrylate, silicon resin, melamine resin, ultraviolet ray-hardenable resin, electron beam-hardenable resin, catalyst-hardenable resin, thermohadenable resin or the like), crystal materials (for example, lithium niobate, lithium tantalate, sapphire, KDP, ADP, calcite or the like), liquid in a transparent container, and a biological tissue (for example, the cornea, the crystal lens, the nail or the like). It is not always necessary that the front and rear surfaces of the object 4 to be measured have mirror surfaces, but the measurement is possible even though it has a rough surface. Further, the object 4 to be measured should not be limited to glass, polymer and crystal material as mentioned above, but a multilayer film thereof may be also used for the object 4 to be measured. Further, the object 4 to be measured, may be a medium which cannot completely absorb light, including a scattering medium in which a scattering agent is mingled, and which can extract and measure reflected rectilinear light. Further, it is not always necessary that the object 4 to be measured is a plane parallel plate, and accordingly, a medium having a front surface and a rear surface which are inclined or curved can be measured.

The drive means 5 holds and mounts thereon the object 4 to be measured, for displacing the object 4 to be measured, in the direction of the optical axis. As to the drive means 5, a slight motion stage such as a pulse stage or a linear motor stage can be used. In order to enhance the accuracy of measurements, these slight motion stages preferably have properties including a resolution of less than 1 $\mu$m, a degree of repeated positioning accuracy of less than 1±$\mu$m, a straightness of less than 1 $\mu$m, a degree of parallelism of less than 1 $\mu$m, a yawing of less then 5 sec. and a pitching of less than 5 sec. It is noted that the drive means 5 should not be limited to the above-mentioned slight motion stages, but may include any of those which can satisfy the above-mentioned properties.

The reference light mirror 6 reflects light branching from light emitted from the light source 1, at the branching and synthesizing means 2. The reflected light (reference light) from the reference light mirror 6 is led to the light receiving element 10 through the branching and synthesizing means 2. As to the reference light mirror 6, a chrome total reflection mirror, an aluminum total reflection mirror, a dielectric multilayer film total reflection mirror or the like may be used, but should not limited in particular thereto. The area and thickness of the reference light mirror 6 are preferably optimized in accordance with a beam diameter irradiated onto the reference light mirror 6, and a force generated by the vibrator 9 for phase-modulating irradiated light. The area is preferably less than the value which is three times as large as the beam diameter of the light irradiated onto the reference light mirror (if the beam diameter is 8 mm, the area is less than 24 mm diameter). The thickness is preferably less than 1 mm. It goes without saying that optimization of the reference light mirror 6 is required in order to maximize the reflecting characteristic thereof in view of a wavelength of the light source 1.

The drive means 7 holds and mounts thereon the reference light mirror 6 for displacing the reference light mirror 6 in the direction of the optical axis. As to the drive means 7, a slight motion stage such as a pulse stage, a linear motor stage or the like may be used. In order to enhance the accuracy of measurement, these slight motion stages preferably have properties including a resolution of less than 1 $\mu$m, a degree of repeated positioning accuracy of less than 1±$\mu$m, a straightness of less than 1 $\mu$m, a degree of parallelism of less than 1 $\mu$m, a yawing of less then 5 sec. and a pitching of less than 5 sec. It is noted that the drive means 7 should not be limited to the above-mentioned slight motion stages, but may include any of those which can satisfy the above-mentioned properties.

The drive means 8 holds and mounts thereon the converging lens 3 for displacing the converging lens 3 in the direction of the optical axis. As to the drive means 8, a slight motion stage such as a pulse stage, a linear motor stage or the like may be used. In order to enhance the accuracy of measurement, these slight motion stages preferably have properties including a resolution of less than 1 $\mu$m, a degree of repeated positioning accuracy of less than 1±$\mu$m, a straightness of less than 1 $\mu$m, a degree of parallelism of less than 1 $\mu$m, a yawing of less then 5 sec. and a pitching of less than 5 sec. It is noted that the drive means 8 should not be limited to the above-mentioned slight motion stages, but may include any of those which can satisfy the above-mentioned properties.

The vibrator 9 phase-modulates light irradiated onto the reference light mirror 6, and during phase-modulation, vibration having an amplitude which is less than $\lambda c/2$ where $\lambda c$ is the oscillating center wavelength of the light source 1, and a frequency of higher than 100 Hz. As to the vibrator 9, a piezo-electric actuator (for example, a laminated film type piezo-electric actuator, a bimorph type piezo-electric actuator, a monomorph type piezo-electric actuator or the like) or an electro-magnetic actuator (for example, a voice coil or the like) may be used. Inter alia, the laminated film type piezo-electric actuator is preferably used since it can exhibit a large displacement at a low voltage, a large generating force and a satisfactory responsiveness while it is small-sized and lightweight. For selection of the vibrator 9, it goes without saying that the oscillating center frequency $\lambda c$ of the used light source and the area and thickness (weight) of the reference light source are important parameters. That is, it is required to select an optimum vibrator in view of the oscillating center wavelength $\lambda c$ and the specification of the reference light mirror 6. In the present invention, the vibrator 9 should not be limited to a piezo-electric actuator (for example, a laminated film type piezo-electric actuator, a bimorph type piezo-electric actuator, a monomorph type piezo-electric actuator or the like) or an electromagnetic actuator (for example, a voice coil or the like) as mentioned above, but may includes any of those which can stably phase-modulate the light irradiated onto the reference light mirror 6 with a predetermined amplitude at a predetermine frequency.

The light receiving element 10 receives reflected light (signal light) from the object 4 to be measured, and reflected light (reference light) from the reference light mirror 6 which are synthesized by the branching and synthesizing means 2. As to the light receiving element 10, a silicon photodiode, a silicon PIN photodiode, a silicon avalanche photodiode, GaAsP photodiode (diffusion type), GaAsP photodidode (shot-key type), GaP photodiode, Ge photodiode, Ge avalanche photodiode, InGaAs-PIN photo-diode or the like may be used. It goes without saying that optimum selection of a light receiving element is required in view of the light wavelength, the output intensity and the phase-modulation frequency of the light source 1. Inter alia, a silicon photo diode is preferable for detection of light having a wavelength from 400 nm to 1,000 nm, or a Ge photodiode is preferable for 700 nm to 1,700 nm. It is noted that the light receiving element 10 should not be limited to a silicon diode, a silicon PIN photodiode, a silicon avalanche photo diode, GaAsP photodiode (diffusion type), GaAsP photodidode (shot-key type), GaP photodiode, Ge photodiode, Ge avalanche photodiode, InGaAs-PIN photo-diode or the like, but may include any of those which can heterodyine-detect the reference light from the reference light mirror 6 and the signal light from the object 4 to be measured which are phase-modulated.

The detecting circuit 11 converts an analog detection signal from the light receiving element 10 into a digital signal. In detail, the detecting circuit 10 is composed of an amplifier, a low-pass/high-pass filter, a sampling hold circuit, and an A/D converter. A signal from the light receiving element 10 is a small signal, and accordingly, is inputted into the amplifier as an amplifying circuit in order to increase an S/N ratio. An output signal from the amplifier, contains noise components from the outside or a power source, and accordingly, the noise components are removed by the low-pass/high-pass filter. An output from the low-pass/high-pass filter is delivered to the sample-hold circuit where a required analog signal for vibrating the vibrator 9 at a predetermined cycle period is held for detecting the signal in synchronization with the cycle period. The held signal is converted into a digital signal by the A/D converter, and accordingly, a desired analog signal can be detected. Data which has been converted from the analog signal into the digital signal by the A/D converter, is taken in to the personal computer PC 13. It is noted here that the detecting circuit 10 incorporates an analog/digital converting function in this case, but the PC 13 may exhibit such an analog and digital conversion. Further, the light receiving element 11 should not be limited to the one having the above-mentioned but the one which also may include any of those which can process data before the detection signal from the light receiving element 10 is taken into the PC.

The lens 12a collimates light from the light source 1 and then directs the light onto the branching and synthesizing means 2. As to the lens, a plano-convex lens, a biconvex lens, a cylindrical lens, a spherical lens or the like which is made of glass, inorganic materials such as optical crystal or polymer materials such as polymethyl-methaacrylate (PMMA) or polycarbonate (PC) can be used as the converging lens 3. Inter alia, a lens made of an inorganic material such as a lens made of BK7 having a high transmissivity for wavelength in an ultraviolet ray range and a near-infrared ray range, or a lens made of quartz having properties including g a high transmissivity for wavelengths in a ultraviolet ray range, a visual light range and a near-infrared ray range, a low thermal expansion coefficient and a thermal stability is preferably used as the lens 12a. The lens 12a is preferably coated with an antireflection (AR) coating in order to decrease the reflection of incident light as possible as it can so as to increase the volume of transmitted light. As to the AR coating, a multilayer coating is preferably used. An objective lens used for a metal microscope may be used as the lens 12a.

The lens 12b directs the reference light from the reference light mirror 6 and the signal light from the object 4 to be measured, which have been synthesized by the branching and synthesizing means 2, to the light receiving element 10. As to the lens, a plano-convex lens, a biconvex lens, a cylindrical lens, a spherical lens or the like which is made of glass, inorganic materials such as optical crystal or polymer materials such as polymethyl-methaacrylate (PMMA) or polycarbonate (PC) can be used as the converging lens 3. Inter alia, a lens made of an inorganic material such as a lens made of BK7 having a high transmissivity for wavelength in an ultraviolet ray range and a near-infrared ray range, or a lens made of quartz having properties including g a high transmissivity for wavelengths in a ultraviolet ray range, a visual light range and a near-infrared ray range, a low thermal expansion coefficient and a thermal stability is preferably used as the lens 12b. The lens 12b is preferably coated with an antireflection (AR) coating in order to decrease the reflection of incident light as possible as it can so as to increase the volume of transmitted light. As to the AR coating, a multilayer coating is preferably used. An objective lens used for a metal microscope may be used as the lens 12b.

The PC 13 controls the drive means 4, 7, 8 through the intermediary of the stage controller 14, and receives optical interference data from the detecting circuit 11, and positional data from the stage controller 14. In detail, it specifies a peak value of maximum interference light intensities at the rear surface of the object 4 to be measured, in accordance with a signal from the detecting circuit 11, and, in this condition, detects the positions of the object 4 to be measured (drive means 5: z=0) or the converging lens 3 (drive means 8: z=0) and the reference light mirror 6 (drive means 7: $x=x_{F1}$ or $x=x_{F2}$) in accordance with data from the stage controller 14. Using these positions as references, a peak value of maximum interference light intensities is specified at the rear surfaces of the object 4 to be measured, and further, in this condition, the positions of the object 4 to be measured (drive means 5: $z=z_1$) or the converging lens 3 (drive means 8: $z=z_2$) and the reference mirror 6 (drive means 7: $x=x_{R1}$ or $x=x_{R2}$) in order to obtain displaced distances of the object 4 to be measured (drive means 5), the converging lens 3 (drive means 8) and the reference light lens 6 (drive means 7) from the front and rear surfaces of the object 4 to be measured. Among these displaced distances thus obtained, that is, the displaced distances of the object 4 to be measured (drive means 5) and the reference light mirror 6 (drive means 7) correspond to $z_1$ and $\Delta L_1 = x_{R1} - x_{F1}$ in the case of the sample displacing process, and the displaced distances of the converging lens 3 and the reference mirror 6 correspond to $z_2$ and $\Delta L_2 = x_{R2} - x_{F2}$. The independent measured values $z_1$, $\Delta L_1$ and $z_2$, $\Delta L_2$ and $NA(=\zeta)$ of the converging lens 3 are substituted in EQ20, EQ21 or EQ36 and EQ37 so as to calculate the phase index np and the thickness t of the object 4 to be measured is calculate. Further, the value of NA(=ζ) of the converging lens 3 is substituted in EQ16, EQ17 or EQ32 and EQ33 so as to calculate the phase index np and the group index ng of the object 4 to be measured. As to the PC 13, any of those which can process data from the above-mentioned detecting circuit 11 and the stage controller 14 can be used without being limited any special one. Further, The function of the PC should not be limited to the process of data, but includes the function of analog-digital conversion which is carried by the detecting circuit 11.

The stage controller 14 precisely controls the drive means 5, 7, 8 in accordance with a signal from the PC13, and obtains precise positional data therefrom. Accordingly, it is required to select an optimum stage controller 14 in view of resolution, positioning accuracy and the like of the drive means 5, 7, 8 used. However, any of those which can control the drive means 5, 7, 8 without being limited to any special one.

In general, a semiconductor laser diode (LD) for optical communication has a narrow oscillating wavelength spectrum width $\Delta\lambda$(<0.1 nm) and is a high quality monochromatic light source. On the contrary, a superluminescent diode (SLD) has a nature which is intermediate of those of a light emitting diodes (LED) and LD. Commercially available SLDs have a wide oscillating wavelength spectrum, $\Delta\lambda$=~about 15 nm. An inteferometric system using a light source such as an SLD having a wide oscillating wavelength spectrum width is the so-called low coherence interferometric optical system, and has a very small coherent length of $\Delta lc=10\ \mu m$. In such an SLD interference optical system, two branching beams (signal light and reference light) from the branching and synthesizing means cannot interfere with each other unless they give a difference (optical pass difference) between their light transmission lengths (optical pass lengths) which is less than about 10 $\mu m$. In other words, the low coherence interferometric optical system can recognize a difference between light transmission paths (optical path lengths) with a resolution of less than about 10 $\mu m$. From this fact, this low coherent interferometric optical system can be used for measuring an optical path length having a resolution in the order of 10 $\mu m$ or for diagnosing a microscopic area. Thus, it can be expected that the present invention can be applied to various kinds of technical fields including industrial fields and medical fields. In particular, with the application to the medical fields including the ophthalmic field, the present invention can be used for various kinds of diagnosis.

Explanation will be made of reference examples of the present invention.

Reference Example 1

In this reference example, a super-luminescent diode (SLD) having an oscillating center wavelength λc of 850 nm was used as the light source 1 shown in FIG. 1. The full width at half maximum (FWHM) of the spectrum of this SLD was $\Delta\lambda$=24 nm from which the coherent length of an interferometer is determined to $\Delta lc=6.6\ \mu m$. Further, a beam splitter (BS), a spherical lens (20×), 0.1 $\mu m$/step linear motor stages (manufactured by Chuoseiki Co., Ltd. ALS902-HIL), and a laminated type piezoelectric actuator (manufactured by Sumitomo Metal Co., Ltd.) were used respectively as the branching and synthesizing means 2, the converging lens 3, the drive means 5, 7 and the vibrator 9. The vibrator 9 was excited with vibration having an amplitude of λc/2 at a frequency f=500 Hz so as to phase-modulate reflected light (reference light) from the reference light mirror 6, and reflected light (signal light) from the object 4 to be measured and the reference light from the reference light mirror 6 were synthesized for interference and heterodyne-detected by an Si-photodiode used as the light receiving element 10. The thus obtained detection signal was converted into a digital signal which was delivered to and processed by the PC so as to specify $\Delta L_1$ and $z_1$ (by the sample displacing process). Further, objective lens (20× and 5×) were used as the lenses 12a, 12b.

Further, a molten quartz plate having a thickness t (=1,026 $\mu m$) and np (=1.4525) which are known was used so as to calibrate the NA (=ζ) of the converging lens 3.

$z_1$ (=703 $\mu m$) was measured in the sample displacing process, and with the use of EQ14, a calibration value ζ=0.134 was obtained.

Then, the constants a, b in EQ13 were determined. Several kinds of transparent materials (solid materials: quartz, BaCD14, FD60, soda glass and LiNbO$_3$(no), and liquid materials: water, glycerin, ethanol and ZEP520) having a known thickness t were used as the object 4 to be measured, and their ng and np were simultaneously measured in accordance with ζ obtained by EQ14 as mentioned above. The results of the measurements are shown in Table 1 and FIG. 9 in which δn is a difference between ng and np.

TABLE 1

Measurement of np, ng by Single SLD
(ζ = 0.134 Calibrated by Quartz)

| | | Solid Material | | | | |
|---|---|---|---|---|---|---|
| | | Quartz | BaCD14 | FD60 | Soda Glass | LiNbO$_3$ (no) |
| Theoretical Value | np | 1.4525 | 1.5947 | 1.7816 | — | 2.2494 |
| | ng | 1.4657 | 1.6123 | 1.825 | — | 2.3411 |
| | δ n[×10$^{-3}$] | 9.13 | 11.03 | 24.34 | — | 40.81 |
| | t[$\mu m$] | 1026 | 1008 | 1060 | 1093 | 1028 |
| Measured Value | $\Delta L_1$[$\mu m$] | 795 | 995 | 1345 | 955 | 1935 |
| | $z_1$[$\mu m$] | 703.0 | 627.8 | 589.0 | 717.8 | 453.2 |
| Calculated Value | np | — | 1.5968 | 1.7885 | 1.5149 | 2.2518 |
| | Δnp | — | 0.13% | 0.38% | — | 0.11% |
| | ng | 1.4600 | 1.6099 | 1.8245 | 1.5305 | 2.3232 |
| | Δng | -0.39% | -0.15% | -0.03% | — | -0.76% |
| | δ n[×10$^{-3}$] | 5.16 | 8.24 | 20.17 | 10.30 | 31.71 |
| | Δδn | -43% | -25% | -17% | — | -22% |

| | | Liquid Material | | | |
|---|---|---|---|---|---|
| | | Water | Glycerine | Ethanol | ZEP520 |
| Theoretical Value | np | 1.329 | — | — | — |
| | ng | 1.3403 | — | — | — |
| | δ n[×10$^{-3}$] | 8.51 | — | — | — |
| | t[$\mu m$] | 1100 | 1126 | 1107 | 1105 |
| Measured Value | $\Delta L_1$[$\mu m$] | 650 | 905 | 695 | 1020 |
| | $z_1$[$\mu m$] | 825.0 | 765.6 | 814.8 | 713.8 |
| Calculated Value | np | 1.3281 | 1.4636 | 1.353 | 1.5399 |
| | Δnp | -0.07% | — | — | — |
| | ng | 1.3409 | 1.4837 | 1.3639 | 1.569 |
| | Δng | 0.04% | — | — | — |
| | δ n[×10$^{-3}$] | 9.64 | 13.73 | 8.06 | 18.90 |
| | Δδn | 13% | — | — | — |

From the results of the simultaneous measurements for the phase index np and the group index ng shown in Table 1, errors between theoretical values and calculated values (Δnp and Δng) for the above-mentioned materials were less than 0.8%, and accordingly, the simultaneous measurement of the phase index np and the group index ng could be carried out with a high degree of accuracy.

Figure 9:
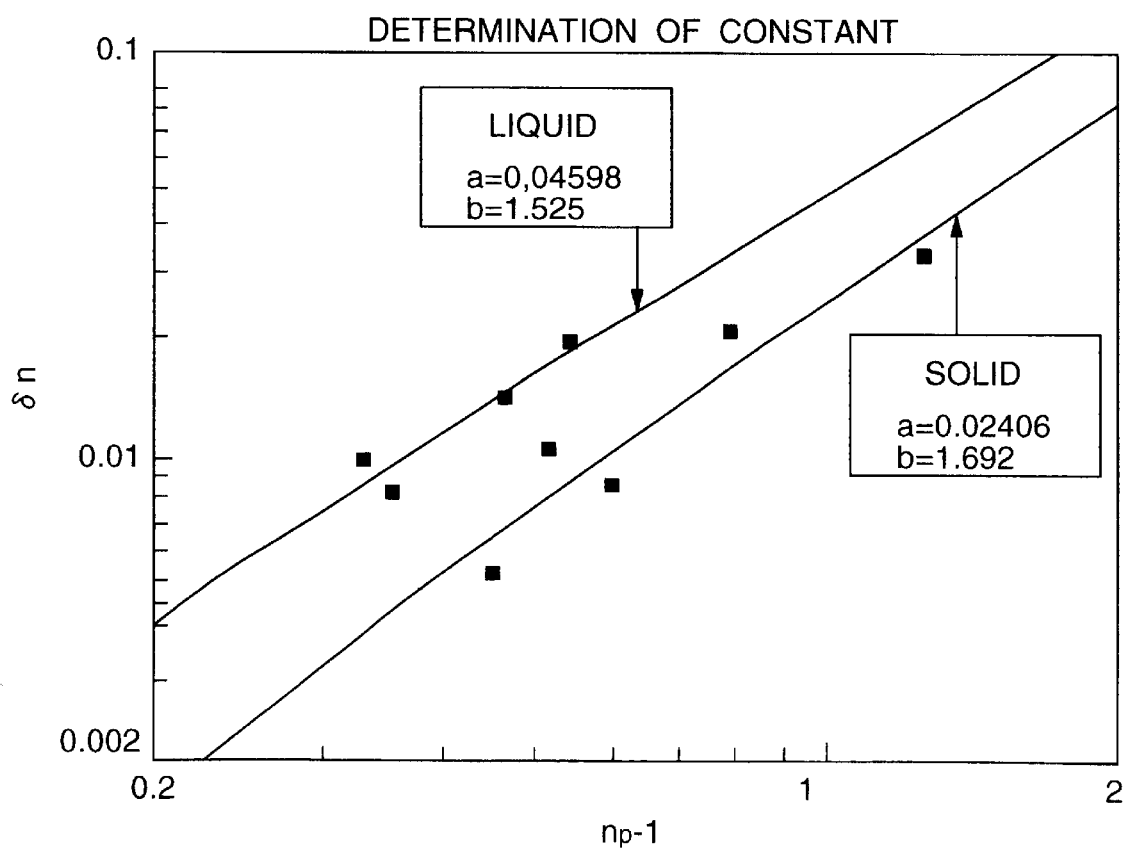
FIG. 9 is a view for explaining determination of constants a, b in an embodiment of the present invention.

Referring to FIG. 9, if a straight line is drawn by the least-square for all measured points, it is found that the measured points of the solid materials are distributed along the straight line. The simultaneous measurement were also made for the liquid materials, and it was expected that the measured points of the liquid materials would be distributed along another straight line.

The straight line obtained by the least square, the following results were obtained:
for the solid materials
    $a=2.406\times10^{-2}$, $b=1.692$;
for the liquid materials
    $a=4.598\times10^{-2}$, $b=1.525$;

From the constants a, b for the solid and liquid materials, obtained from the above-mentioned experiments, the values $z_1$ and $\Delta L_1$ of the molten quartz plate were used, and the phase index $np=1.4329$ of water was used for the liquid materials, $NA(=\zeta i)$ of the converging lens 3 was calibrated by EQ19:

Solid materials: $\zeta i=0.114$
    Liquid material: $\zeta i=0.123$

In addition to the value of $NA(\zeta i=0.114)$ of the spherical lens calibrated with the molten quartz plate, the measured values of $z_1$, $\Delta L_1$ of the several kinds of the objects 4 to be measured were substituted in EQ13, EQ20 and EQ21, in order to calculate the phase refractive indices np and the thicknesses t. Results are shown in Table 2.

TABLE 2

Calculated Value np, t Added with Correction Term ($\zeta_1 = 0.114$)

| | | Solid Material | | |
|---|---|---|---|---|
| | | Sapphire | LiNbO$_3$ (ne) | LiTaO$_3$ (no) |
| Theoretical Value | np | 1.7589 | 2.1706 | 2.1501 |
| | t[μm] | 997 | 1028 | 496 |
| Measured Value | $\Delta L_1$[μm] | 1208 | 1825 | 865 |
| | $z_1$[μm] | 564.0 | 469.2 | 228.4 |
| Calculated Value | np | 1.7547 | 2.1679 | 2.1463 |
| | $\Delta$np | −0.24% | −0.12% | −0.17% |
| | t[μm] | 994.0 | 1022.4 | 492.7 |
| | $\Delta$t | −0.30% | −0.54% | −0.66% |

| | | Vinyl Chloride | Acrylic | Styrene | FDS1 |
|---|---|---|---|---|---|
| Theoretical Value | t[μm] | 1051 | 2020 | 1506 | 1067 |
| Measured Value | $\Delta L_1$[μm] | 945 | 1665 | 1460 | 1406 |
| | $z_1$[μm] | 681.6 | 1355 | 945.8 | 568.8 |
| Calculated Value | np | 1.5352 | 1.4848 | 1.5837 | 1.8654 |
| | t[μm] | 1050.4 | 2019.1 | 1503.7 | 1066.0 |
| | $\Delta$t | −0.06% | −0.04% | −0.15% | −0.10% |

Errors of np was less than 0.7% as to sapphire, X-cut LiNbO$_3$ and LiTaO$_3$, and errors of t was less than 0.3%. Further, the measurement was made to optical glass (FSD1), vinyl chloride plates, acrylic plates, and styrene plate having unknown theoretical values of np, and errors between the results of the measurement and actual measured values of t with the use of a micrometer gage were less than 0.2%.

Reference Example 2

In this reference example, a super-luminescent diode (SLD) having an oscillating center wavelength λc of 850 nm was used as the light source 1 shown in FIG. 1. The full width at half maximum (FWHM) of the spectrum of this SLD was adjusted, as was similar to the reference example 1, to $\Delta\lambda=24$ nm from which the coherent length of an interferometer is determined to $\Delta lc=6.6$ μm. Further, an Aluminum half mirror, a spherical lens (20×) as is similar to the reference example 1, 0.1 μm/step linear motor stages (manufactured by Chuoseiki Co., Ltd. ALS902-HIL), and a laminated type piezoelectric actuator (manufactured by Tohkin Co., Ltd.) were used respectively as the branching and synthesizing means 2, the converging lens 3, the drive means 5, 8 and the vibrator 9. The vibrator 9 was excited with vibration having an amplitude of λc/2 at a frequency $f=500$ Hz so as to phase-modulate reflected light (reference light) from the reference light mirror 6, and reflected light (signal light) from the object 4 to be measured and the reference light from the reference light mirror 6 were synthesized for interference and heterodyne-detected by an Si-photodiode used as the light receiving element 10. The thus obtained detection signal was converted into a digital signal which was delivered to and processed by the PC so as to specify $\Delta L_2$ and $z_2$ (by the lens displacing process). Further, objective lens (20× and 5×) were used as the lenses 12a, 12b.

As to $NA(\zeta)$ and the constants a, b, the values which were calibrated in the reference example 1 were used.

X-cut LiNbO$_3$ as the object 4 to be measured was measured so as to measure a birefringence (normal light: $n_o$, and abnormal light: n) $z_2$, and $\Delta L_2$, and thus obtained values are substituted into EQ36, EQ37 and EQ38, EQ40, EQ41 in order to calculate the phase index np and the group index ng, and the phase index np and the thickness t. The results of the calculation are shown in Table 3.

TABLE 3

Result of Simultaneous Measurement of np and ng, np and t

| | | LiNbO$_3$ (no) | LiNbO$_3$ (ne) |
|---|---|---|---|
| *Measurement of np, ng by Single SLD $\zeta = 0.134$ | | | |
| Theoretical Value | np | 2.2494 | 2.1706 |
| | ng | 2.3411 | 2.2497 |
| | t[μm] | 1028 | 1028 |
| Measured Value | $\Delta L_2$[μm] | 2388 | 2294.2 |
| | $z_2$[μm] | 453.2 | 469.0 |
| Calculated Value | np | 2.2518 | 2.1763 |
| | $\Delta$np | 0.11% | 0.26% |
| | ng | 2.3230 | 2.2317 |
| | $\Delta$ng | −0.77% | −0.80% |
| *Calculated Value np, t Added with Correction Term $\zeta_1 = 0.114$ | | | |
| Theoretical Value | np | 2.2493 | 2.1706 |
| | t[μm] | 1028 | 1028 |
| Measured Value | $\Delta L_2$[μm] | 2388 | 2294.2 |
| | $z_2$[μm] | 453.2 | 469.0 |
| Calculated Value | np | 2.2455 | 2.1683 |
| | $\Delta$np | −0.17% | −0.10% |
| | t[μm] | 1023.0 | 1022.2 |
| | $\Delta$t | −0.48% | −0.56% |

From the results of the simultaneous measurements for the phase index np and the group index ng, errors were less than 0.8% as to $n_e$, $n_o$ of the X-cut LiNbO$_3$, and as to the results of simultaneous measurement of the phase index np and the thickness t, errors for the phase index np were less than 0.2% while errors for the thickness t were less than 0.6%.

Reference Example 3

In this reference example, Superluminscdent diode (SLD) having an oscillating center wavelength λc of 850 nm was used as the light source 1 shown in FIG. 1. The full width at half maximum (FWHM) of the spectrum of this SLD was, $\Delta\lambda=24$ nm from which the coherent length of an interferometer is determined to $\Delta lc=6.6$ $\mu$m. Further, a beam splitter (BS), a spherical lens (20×) as is similar to the reference example 1, 1 $\mu$m/step pulse stage stages (manufactured by Chuoseiki Co., Ltd. MN-60X), and a laminated type piezoelectric actuator (Sumitomo Metal Co., Ltd.) were used respectively as the branching and synthesizing means 2, the converging lens 3, the drive means 5, 7 and the vibrator 9. The vibrator 9 was excited with vibration having an amplitude of $\lambda c/2$ at a frequency f=500 Hz so as to phase-modulate reflected light (reference light) from the reference light mirror 6, and reflected light (signal light) from the object 4 to be measured and the reference light from the reference light mirror 6 were synthesized for interference and heterodyne-detected by an Si-photodiode used as the light receiving element 10. The thus obtained detection signal was converted into a digital signal which was delivered to and processed by the PC so as to specify $\Delta L_1$ and $z_1$ (by the sample displacing process). Further, objective lens (20× and 5×) were used as the lenses 12$a$, 12$b$.

It is noted that NA($\zeta$, $\zeta i$) of the converging lens 3 and the constants a, b, the values which were calibrated in the reference example 1 were used.

Human Nail as the object 4 to be measured was measured, and as a result, $z_1=242$ $\mu$m, and $\Delta L_1=303$ $\mu$m were obtained. From these measured values, a refractive index np=1.4924 and thickness t=362.5 $\mu$m were obtained.

The above-mentioned results were substantially identical with thickness measured with the use of a micrometer, and accordingly, it was found that the simultaneous measurement of the phase index np and the thickness t can be made with a high degree of accuracy.

Reference Example 4

In this reference example, light having an oscillating center wavelength $\lambda c$ of 850 nm obtained by spectroscopy (spectrometer SM-3 manufactured by Spectrometer Co., Ltd) of light from xenon lamp with the use of a monochromator was used as the light source 1 shown in FIG. 12. The full width at half maximum (FWHM) of the spectrum of this SLD was adjusted, as is similar to the reference example 1, to $\Delta\lambda=24$ nm from which the coherent length of an interferometer is determined to $\Delta lc=6.6$ $\mu$m. Further, a single mode fiber coupler, a 0.1 $\mu$m/linear motor stage (manufactured by Chuoseiki Co., Ltd. ALS902-HIL), X-cut LiNbO$_3$ (LN) having a crystal axis perpendicular to the surface, and a bimorph piezoelectric actuator (Sumitomo Metal Co., Ltd.) were used respectively as the branching and synthesizing means 2, the drive means 5, the object 4 to be measured and the vibrator 9. The vibrator 9 was excited with vibration having an amplitude of $\lambda c/2$ at a frequency f=1 kHz so as to phase-modulate reflected light (reference light) from the reference light mirror 6, and reflected light (signal light) from the object 4 to be measured and the reference light from the reference light mirror 6 were synthesized for interference and heterodyne-detected by an Si-photodiode used as the light receiving element 10. The thus obtained detection signal was converted into a digital signal which was delivered to and processed by the PC so as to specify $z_3$ ($n_o$) and $z_3$ ($n_e$) (by the sample displacing process). Then, with a known thickness t, the birefringence of X-cut LN was evaluated. Further, objective lens (20× and 5×) were used as the lenses 12$a$, 12$b$. The light input and outputs ports of the single mode optical fiber coupler were provided with 20× objective lenses, respectively, so that incident light to the fiber coupler was converged to a mode field diameter of the fiber in order to optimize the efficiency of coupling with the fiber. Meanwhile the emanating light was collimated into a beam having 6 mm diameter which was then led to the reference light mirror 6 and the lens 12$b$.

As a result, an optical path length (1)(=$n_o$×t)=2388.2 $\mu$m for normal light, and an optical path length $z_3$ (2) (=$n_e$×t)= 2,294 $\mu$m were obtained, and $\Delta n \times t=|n_o-n_e|\times t=94$ $\mu$m was also obtained. Since these values were dependent upon the phase index np, a group index $n_og=2.3232$ for the normal light, and $n_eg=2.2317$ and $\Delta ng=0.0915$ were obtained from a thickness t=1.028 $\mu$m measured by a micrometer.

The above-mentioned results are greatly coincident with the theoretical group refractive indices ($n_eg=2.3411$, $n_eg=2.2497$, $\Delta ng=0.0914$) based upon Sellmeir's equation in consideration with wavelength dispersion. Accordingly, a birefringence could be measured with a high degree of accuracy of less than 0.2%.

Reference Example 5

In this reference example, light having an oscillating center wavelength $\lambda c$ of 850 nm obtained by spectroscopy (spectrometer SM-3manufactured by Spectrometer Co., Ltd.) of light from xenon lamp with the use of a monchromator was used as the light source 1 shown in FIG. 12. The full width at half maximum (FWHM) of the spectrum of this SLD was adjusted, as is similar to the reference example 1, to $\Delta=24$ nm from which the coherent length of an interferometer is determined to $\Delta lc=6.6$ $\mu$m. Further, a single mode fiber coupler, a 0.1 $\mu$m/linear motor stage (manufactured by Chuoseiki Co., Ltd. ALS902-HIL), X-cut LiNbO$_3$ (LN) having a crystal axis perpendicular to the surface, and a bimorph piezoelectric actuator (Sumitomo Metal Co., Ltd.) were used respectively as the branching and synthesizing means 2, the drive means 5, the object 4 to be measured and the vibrator 9. The vibrator 9 was excited with vibration having an amplitude of $\lambda c/2$ at a frequency f=1 kHz so as to phase-modulate reflected light (reference light) from the reference light mirror 6, and reflected light (signal light) from the object 4 to be measured and the reference light from the reference light mirror 6 were synthesized for interference and heterodyne-detected by an Si-photodiode used as the light receiving element 10. The thus obtained detection signal was converted into a digital signal which was delivered to and processed by the PC so as to specify $\Delta L_3(n_o)$ and $\Delta L_3(n_e)$ (by the reference light mirror displacing process). Then, with a known thickness t, the birefringence of X-cut LN was evaluated. Further, objective lenses (20× and 5×) were used as the lenses 12$a$, 12$b$. An objective lens (20×) is used for each of inlet and outlet ports of the coupler. Incident light to the fiber coupler was converged to a mode field diameter of the fiber in order to optimize the efficiency of coupling with the fiber. Meanwhile the emanating light was collimated into a beam having 6 mm diameter which was then led to the reference light mirror 6 and the lens 12$b$.

As a result, an optical path length $\Delta L_3(1)$ (=$n_o$×t)=2388.1 $\mu$m for ordinary light rays, and an optical path length $\Delta L_3(2)$ (=$n_e$×t)=2,293.9 $\mu$m were obtained, and $\Delta n \times t=|n_o-n_e|\times t=94.2$ $\mu$m was also obtained. Since these values were dependent upon the phase index ng, a group index $n_og=2.3231$ for the ordinary light rays, $n_eg=2.2314$ for extraordinary light rays and $\Delta ng=0.0917$ were obtained from a thickness t=1.028 $\mu$m measured by a micrometer.

The above-mentioned results are greatly coincident with the theoretical group refractive indices ($n_eg=2.3411$, $n_eg=$ 2.2497, Δng=0.0914) based upon Sellmeir's equation in consideration with wavelength dispersion. Accordingly, a birefringence could be measured with a high degree of accuracy of less than 0.4%.

Reference Example 6

In this reference example, Superluminscdent diode (SLD) having an oscillating center wavelength λc of 850 nm was used as the light source 1 shown in FIG. 1. The full width at half maximum (FWHM) of the spectrum of this SLD was Δλ=24 nm from which the coherent length of an interferometer is determined to Δlc=6.6 μm. Further, a beam splitter (BS), a spherical lens (20×) as is similar to the reference example 1, 0.1 μm/step linear motor stages (manufactured by Chuoseiki Co., Ltd. ALS902-HIL), and a laminated type piezoelectric actuator (Sumitomo Metal Co., Ltd.) were used respectively as the branching and synthesizing means 2, the converging lens 3, the drive means 5, 7 and the vibrator 9. The vibrator 9 was excited with vibration having an amplitude of λc/2 at a frequency f=500 Hz so as to phase-modulate reflected light (reference light) from the reference light mirror 6, and reflected light (signal light) from the object 4 to be measured and the reference light from the reference light mirror 6 were synthesized for interference and heterodyne-detected by an Si-photodiode used as the light receiving element 10. The thus obtained detection signal was converted into a digital signal which was delivered to and processed by the PC so as to specify $\Delta L_1$ and $z_1$ (by the sample displacing process). Further, objective lens (20× and 5×) were used as the lenses 12a, 12b.

It is noted that NA(ζ) of the converging lens 3 and the constants a, b, the values which were calibrated in the reference example 1 were used.

Ultraviolet ray-hardenable resin (manufactured by Kansai Paint Co.) which with different ultraviolet ray exposure rates, as the object 4 to be measured was measured, and measured values $z_1$, $\Delta L_1$ of the object 4 to be measured obtained each of the measurements with different ultraviolet exposure rates were substituted into EQ13, EQ20 and EQ21 so as to calculate a phase index np and a thickness. Results of the calculation and results of measuring gel fractions of the same samples are shown in Table 4 and FIG. 18. It is noted that the condition of measuring the gel fraction was such as circulation of methyl keton: 2 hours, drying: 105 deg. C. for 1 hour. From these measured values, a refractive index np=1.4924 and thickness t=362.5 μm were obtained.

TABLE 4

Result of Measurement of np, t and Gel Fraction Rate of Ultraviolet Ray - Hardenable Resin

| Ultraviolet Ray Irradiation Intensity [mJ/cm$^2$] | Phase Refractive Index np | Thickness [μm] | Gel Fraction [%] |
|---|---|---|---|
| 0 | 1.4732 | 968.9 | 0 |
| 10 | 1.4784 | 690.3 | 48.8 |
| 20 | 1.4880 | 714.4 | 78.0 |
| 30 | 1.4970 | 738.4 | 80.5 |
| 40 | 1.4948 | 711.7 | 90.7 |
| 50 | 1.4953 | 663.7 | 87.2 |
| 60 | 1.4955 | 728.9 | 88.4 |
| 70 | 1.4937 | 736.8 | 92.6 |
| 80 | 1.4972 | 720.4 | 94.8 |
| 90 | 1.4925 | 660.9 | 86.4 |
| 100 | 1.4958 | 775.5 | 88.6 |

TABLE 4-continued

Result of Measurement of np, t and Gel Fraction Rate of Ultraviolet Ray - Hardenable Resin

| Ultraviolet Ray Irradiation Intensity [mJ/cm$^2$] | Phase Refractive Index np | Thickness [μm] | Gel Fraction [%] |
|---|---|---|---|
| 150 | 1.4945 | 646.7 | 90.7 |
| 200 | 1.4931 | 707.8 | 93.6 |
| 400 | 1.4954 | 651.6 | 95.2 |

From these results, it is found that a hardened condition or hardness of hardenable resin can be easily evaluated with the use of a refractive index in a nondestructive and noncontact manner with a degree of accuracy which is equal to or higher than that obtained by the gel fractions used in conventional evaluation.

Figure 18:
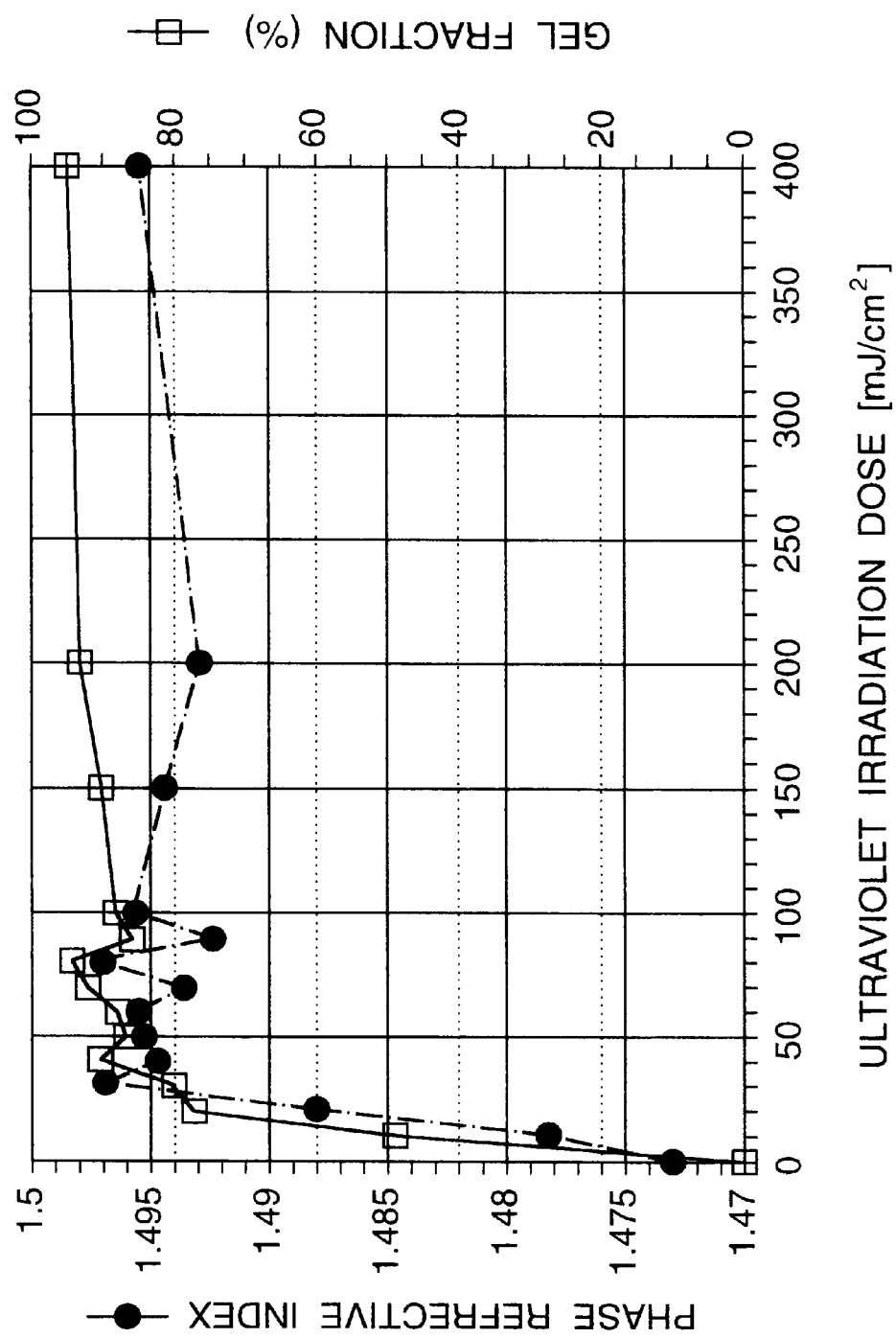
FIG. 18 is a graph showing relationships between phase index and gel fraction of ultraviolet-hardenable resin and ultraviolet irradiation value.

It is considered that unevenness of measured points of phase refractive indices and gel fractions in FIG. 18 are caused by unevenness in preparation of samples with ultraviolet ray exposure doses.

It goes without saying that the center wavelength of the light source, the full width at half maximum of spectrum which have been explained in the references examples as mentioned above, are only of examples, and accordingly other light sources having similar characteristics and other light receiving elements corresponding thereto may be used.

Further, the drive frequency of the actuator or the like should not be limited to the specified one.

Further, the evaluation to a hardened condition or hardness of the ultraviolet ray hardenable resin is one of examples, and the evaluation to various kinds of several hardenable resin can also be made.

The detecting circuit 11 for detecting a signal from the light receiving element 10 may incorporate an amplifier circuit, a filter, a sample-hold circuit and the like as necessary. Further, filter computation can be made by the PC.

According to the present invention as mentioned above, simultaneous measurement of a phase index and a thickness of an object to be measured, simultaneous measurement of a birefringence and a thickness, measurement of a birefringence, and simultaneous measurement of a phase index and a group index can be carried out with a high degree of accuracy with the use of a simple structure optical measuring system in combination of a low coherence interferometric optical system means for driving a reference light mirror, an object to be measured and a converging lens, and a detection signal process, since a converged light beam is irradiated onto the object to be measured, simultaneous measurement of np (including a birefringence) or ng (including a birefringence) and t can be made. Further, since the object to be measured is measured in a matrix-like manner, a spatial distribution of np (including a birefringence) or ng (including a birefringence) and t can also be measured.

Further, with the use of a measuring methods according to the present invention, a hardened condition or a hardness of hardenable resin can be simply measured and evaluated in a nondestructive and noncontact manner with a high degree of accuracy which is equal to or higher than that of the gel fraction which is a conventional evaluation process.

What is claimed is:
1. A measuring method for measuring an optical characteristic of an optically transmissive object having a front surface and a rear surface, using an optical system including a light source for emitting light, a converging lens, a reference light mirror, a light receiving element, drive means for displacing one of (i) the object to be measured and said reference light mirror and (ii) said converging lens and said reference light mirror, said method comprising the steps of:

simultaneously converging said light from the light source through said converging lens, and onto the object, and irradiating said light from the light source onto the reference light mirror;

synthesizing a reflected light beam from the front surface of the object and a reflected light beam from the reference light mirror through interference therebetween into a first synthesized interference light beam, and directing the first synthesized interference light beam into the light receiving element, while synthesizing a reflected light beam from the rear surface of the object to be measured, and a reflected light beam from the reference light mirror through interference therebetween into a second synthesized interference light beam, and directing the second synthesized interference light beam into the light receiving element;

displacing one of (i) the object and the reference light mirror and (ii) the converging lens and the reference light mirror so as to maximize an intensity of each of the first and second interference light beams; and obtaining distances of displacement of said one of (i) the object and the reference light mirror and (ii) the converging lens and the reference light mirror, from a position where an intensity of each of the first and second interference light beams becomes maximum in order to simultaneously measure a refractive index and a thickness of the object to be measured.

2. A measuring method for measuring an optical characteristic of an optically transmissive object having a front surface and a rear surface, using an optical system including a light source for emitting light, a reference light mirror, a light receiving element, drive means for displacing one of the object to be measured and the reference light mirror, said method comprising the steps of:

simultaneously irradiating light from the light source onto the object and onto the reference light mirror;

synthesizing a reflected light beam from the front surface of the object and a reflected light beam from the reference light mirror through interference therebetween into a first synthesized interference light beam and directing the first synthesized interference light beam to the light receiving element;

synthesizing a reflected ordinary light beam from the rear surface of the object and a reflected light beam from the reference light mirror through interference therebetween into a second synthesized interference light beam and directing the second synthesized interference light beam to the light receiving element;

synthesizing a reflected extraordinary light beam from the rear surface of the object and a reflected light beam from the reference light mirror through interference therebetween into a third synthesized interference light beam and directing the third synthesized interference light to the light receiving element;

displacing one of (i) the object and (ii) the reference light mirror so as to maximize an intensity of each of the first, second and third interference light beams; and obtaining a distance of displacement of said one of (i) the object and (ii) the reference light mirror, from a position where each of the first, second and third interference light beams becomes maximum in order to simultaneously measure a birefringence and a thickness of the object to be measured.

3. A measuring method for measuring an optical characteristic of an optically transmissive object having a front surface and a rear surface, using an optical system including a light source for emitting light, a converging lens, a reference light mirror, a light receiving element, a drive means for displacing one of (i) the object and the reference light mirror and (ii) the converging lens and the reference light mirror, said method comprising the steps of:

simultaneously converging said light from the light source through the converging lens and onto the object, and irradiating said light from the light source onto the reference light mirror;

synthesizing a reflected light beam from the front surface of the object and a reflected light beam from the reference light mirror through interference therebetween into a first synthesized interference light beam and directing the first synthesized interference light beam to the light receiving element;

synthesizing a reflected ordinary light beam from the rear surface of the object and a reflected light beam from the reference light mirror through interference therebetween into a second synthesized interference light beam and directing the second synthesized interference light beam to the light receiving element;

synthesizing a reflected extraordinary light beam from the rear surface of the object and a reflected light beam from the reference light mirror through interference therebetween into a third synthesized interference light beam and directing the third synthesized interference light beam to the light receiving element, displacing one of (i) the object and the reference light mirror and (ii) the converging lens and the reference light mirror so as to maximize an intensity of each of the first, second and third interference light beams; and obtaining distances of displacement of said one of (i) the object and the reference light mirror and (ii) the converging lens and the reference light mirror, from a position where each of the first, second and third interference light beams becomes maximum in order to simultaneously measure a birefringence and a thickness of the object to be measured.

4. A measuring method for measuring an optical characteristic of an optically transmissive object having a front surface and a rear surface, using an optical system including a light source for emitting light, a converging lens, a reference light mirror, a light receiving element, drive means for displacing one of (i) the object to be measured and the reference light mirror and (ii) the converging lens and the reference light mirror, said method comprising the steps of:

simultaneously converging said light from the light source through said converging lens and onto the object and irradiating said light from the light source onto the reference light mirror;

synthesizing a reflected light beam from the front surface of the object and a reflected light beam from the reference light mirror through interference therebetween into a first synthesized interference light beam, and directing the first synthesized interference light beam into the light receiving element, while synthesizing a reflected light beam from the rear surface of the object and a reflected light beam from the reference light mirror through interference therebetween into a second synthesized interference light beam, and directing the second synthesized interfering light into the light receiving element;

displacing one of (i) the object and the reference light mirror and (ii) the converging lens and the reference light mirror so as to maximize an intensity of each of the first and second interference light beams; and obtaining distances of displacement of said one of (i) the object and (ii) the converging lens and the reference light mirror, from a position where an intensity of each of the interference light beams becomes maximum in order to simultaneously measure a phase refractive index and a group index of the object to be measured.

5. A method as set forth in claim 1 further comprising applying arithmetic formulae in consideration with a wavelength dispersion of the refractive index of the object to be measured to permit the simultaneous measurement of the refractive index and the thickness and deriving simultaneously the phase index and the thickness of the object.

6. A method as set forth in claim 3 further comprising applying formulae in consideration with a wavelength dispersion of the refractive index of the object to be measured to permit the simultaneous measurement of the birefringence and the thickness, and deriving simultaneously the phase index and the thickness of the object to be measured.

7. A method as set forth in claim 1 or 4, wherein the light is one for emitting low coherence light.

8. A method as set forth in claim 7, wherein the light source emitting the low coherence light is one of a linearly polarized light source and an unpolarized light source.

9. A method as set forth in claim 7, wherein the light source for emitting the low coherent light is one of a linearly polarized light source, a non-polarized light source and a randomly polarized light source and has a coherence length $\Delta lc$ $(=((\ln(2))\times(2/\pi)\times(\lambda c^2/\Delta\lambda))/2))$ which is less than 30 $\mu$m.

10. A method as set forth in claim 9, wherein the light source for emitting the low coherent light is a white light source whose output is subjected to spectroscopy for a specific wavelength range by a monochrometer.

11. A method as set forth in claim 2 or 3, wherein the light source is one for emitting low coherence light.

12. A method as set forth in claim 11, wherein the light source emitting the low coherence light is a unpolarized light source.

13. A method as set forth in claim 12, wherein the light source for emitting the low coherent light is a super luminescent diode.

14. A method as set forth in claim 11, wherein the light source for emitting the low coherent light is one of a non-polarized light source and a randomly polarized light source and has a coherence length $\Delta lc$ $(=((\ln(2))\times(2/\pi)\times(\lambda c^2/\Delta\lambda))/2)$ which is less than 30 $\mu$m.

15. A method as set forth in claim 14, wherein the light source for emitting the low coherent light is a super luminescent diode.

16. A method as set forth in claim 14, wherein said light source for emitting the low coefficient light is a white light source whose output is subjected to spectroscopy for specific wavelength range by a monochrometer.

17. A method as set forth in claim 1, 2, 3 or 4, wherein said interferometric system includes a means for branching and synthesizing light from the light source.

18. A method as set forth in any one of claims 1, 2, 3 or 4, wherein each of the drive means for displacing said one of the object and the converging lens and said drive means for displacing the reference light mirror comprises a slight motion stage.

19. A method as set forth in claim 1, 2, 3 or 4 wherein the reference light mirror in the interferometric system is secured to a vibrator for vibrating the reference light mirror to phase modulate the reference light.

20. A method as set forth in claim 19, wherein phase-modulation of the reference light is carried out by applying vibration having (i) an amplitude which is less than $\lambda c/2$ where $\lambda c$ is the oscillating center wavelength of the light source, and (ii) a frequency higher than 100 Hz.

21. A method as set forth in claim 1, 2, 3 or 4, wherein the light receiving element is a photodiode for heterodyne detection.

22. A method as set forth in claim 1, 2, 3 or 4, wherein a detection signal subjected to the heterodyne detection is converted into a digital signal by a detecting circuit.

23. A method as set forth in claim 1, 2, 3 or 4, wherein the object is a medium which does not completely absorb light from the light source.

24. A method as set forth in claim 1, 2, 3 or 4 wherein said object is a biological tissue.

25. An apparatus for measuring optical characteristics including refractive index and thickness of a light transmissive object, said apparatus comprising:

a light source for emitting light;

means for splitting said light from the light source into first light and second light;

a reference light mirror for receiving and reflecting one of said first light and said second light;

a converging lens;

means for passing the other one of said first light and said second light through said converging lens onto said object;

means for displacing one of (i) the object and the reference light mirror and (ii) the converging lens and the reference light mirror;

a light receiving element for synthesizing reflected light from the object and reference light from the reference light mirror for interference so as to deliver an interference light signal; and means for applying arithmetic formulae in consideration with a wavelength dispersion of the refractive index of the object for simultaneous measurement of the refractive index and the thickness, so as to simultaneously derive the phase index and the thickness of the object to be measured.

26. An apparatus for measuring birefringence and thickness of an object to be measured, said apparatus comprising:

a light source for emitting light;

means for splitting light from the light source into first light and second light;

a reference light mirror for receiving and reflecting one of said first light and said second light;

a converging lens;

means for passing the other one of said first light and said second light through said converging lens onto said object;

means for displacing one of (i) the object and the reference light mirror and (ii) the converging lens and the reference light mirror;

a light receiving element for synthesizing reflected light from the object and reference light from the reference light mirror for interference so as to deliver an interference light signal; and means for applying arithmetic formulae in consideration with a wavelength dispersion of the object for simultaneous measurement of the birefringence and the thickness, so as to simultaneously derive the phase index and the thickness of the object to be measured.

* * * * *